(12) United States Patent
Marchand et al.

(10) Patent No.: US 9,436,783 B2
(45) Date of Patent: Sep. 6, 2016

(54) METHOD AND SYSTEM FOR ESTIMATING DEGRADATION AND DURABILITY OF CONCRETE STRUCTURES AND ASSET MANAGEMENT SYSTEM MAKING USE OF SAME

(71) Applicant: SIMCO TECHNOLOGIES INC., Quebec (CA)

(72) Inventors: Jacques Marchand, Quebec (CA); Etienne Gregoire, Quebec (CA); Eric Samson, Quebec (CA)

(73) Assignee: SIMCO TECHNOLOGIES INC., Quebec, QC (CA)

( * ) Notice: Subject to any disclaimer, the term of this patent is extended or adjusted under 35 U.S.C. 154(b) by 379 days.

(21) Appl. No.: 14/152,754

(22) Filed: Jan. 10, 2014

(65) Prior Publication Data

US 2014/0249788 A1    Sep. 4, 2014

Related U.S. Application Data

(60) Provisional application No. 61/771,475, filed on Mar. 1, 2013.

(51) Int. Cl.
*G06F 17/50* (2006.01)
*G01N 33/38* (2006.01)
*G01N 21/95* (2006.01)

(52) U.S. Cl.
CPC .......... *G06F 17/5009* (2013.01); *G01N 21/95* (2013.01); *G01N 33/383* (2013.01)

(58) Field of Classification Search
USPC .................................. 703/2, 7; 324/637, 644
See application file for complete search history.

(56) References Cited

U.S. PATENT DOCUMENTS 6,186,006 B1    2/2001    Schmitz et al.
6,246,354 B1    6/2001    Liedtke et al.
(Continued)

OTHER PUBLICATIONS chapter by Der Kiureghian, A. (2005) entitled "First- and second-order reliability methods." in Engineering Design Reliability Handbook, E. Nikolaidis, D. M. Ghiocel, and S. Singhal, eds., CRC Press., 24 pages.
(Continued)

*Primary Examiner* — Thai Phan

(57) ABSTRACT

A method, system and computer program product for estimating degradation and durability characteristics of a reinforced concrete structure are provided. Location-dependent information conveying structural information associated with different locations along the concrete structure is received, the location-dependent information having been obtained by applying a non-destructive testing (NDT) process to the concrete structure. The location-dependent information is processed in combination with information conveying material properties and information conveying estimated environmental conditions to derive concrete degradation simulation data conveying estimated degradation and durability characteristics associated with the different locations along the concrete structure. A signal is then released, causing the estimated degradation and durability characteristics of the concrete structure to be displayed on a display device. Aspects of the proposed approach may be integrated into concrete asset managing systems and be used to assist in managing, including planning maintenance activities in connection with, reinforced concrete structures such as bridges, roadways, ports and the like.

46 Claims, 19 Drawing Sheets

(56) References Cited

U.S. PATENT DOCUMENTS

| | | | |
|---|---|---|---|
| 6,429,802 | B1 | 8/2002 | Roberts |
| 6,959,270 | B2 | 10/2005 | Marchand et al. |
| 7,075,315 | B2 | 7/2006 | Tanaka |
| 7,190,302 | B2 | 3/2007 | Biggs |
| 7,374,006 | B2 | 5/2008 | Boehm |
| 7,937,229 | B2 | 5/2011 | Buyukozturk et al. |
| 2003/0171879 | A1* | 9/2003 | Pittalwala ............... F17D 5/00 702/34 |
| 2004/0189289 | A1* | 9/2004 | Atherton ............ G01N 33/383 324/220 |
| 2004/0243321 | A1* | 12/2004 | Pittalwala ............... F17D 5/00 702/34 |
| 2010/0052971 | A1 | 3/2010 | Amarillas |
| 2013/0338267 | A1* | 12/2013 | Appleby ................ B22C 9/04 523/458 |

OTHER PUBLICATIONS

E. Rosenblueth. "Two-point estimates in probabilities", Applied Mathematical Modeling, 5:329-335, 1981.

FHWA—2010 Status of the Nation's Highways, Bridges, and Transit—Condition & Performance. Technical report, Report to congress, 2010—Exhibit 3-20, 502 pages.

Y.H. Huang, Adams and T.M.Pincheira J.A. "Analysis of life-cycle maintenance strategies for concrete bridge decks", Journal of Bridge Engineering, 9:250-258, 2004.

T.J. Kirkpatrick et al. "Impact of specification changes on chloride-induced corrosion service life of bridge decks", Cement and Concrete Research, 32:1189-1197, 2002.

Y. Liu et al., "Modeling the time-to-corrosion cracking in chloride contaminated reinforced concrete structures", ACI Materials Journal, 95:675-681, 1998.

Examiner's Report issued on Dec. 22, 2015 in connection with Canadian Patent Application No. 2,839,056, 8 pages.

Klinghoffer et al., "Condition assessment of concrete structures at nuclear power plants by state of the art non-destructive testing", EPI web of Conferences, vol. 12, 03002, 10 pages, Apr. 2011.

Van der Wielen et al., "Nondestructive Detection of Delaminations in Concrete Bridge Decks", IEEE 2010 13th International Conference on Ground Penetrating Radar (GPR), 5 pages, Jun. 2010.

Wiggenhauser, "Advanced NTD methods for the assessment of concrete structures", Concrete Repair, Rehabilitation and Retrofitting II: 2nd International Conference ICCRRR-2, Nov. 24-26, 2008, 13 pages.

* cited by examiner

METHOD AND SYSTEM FOR ESTIMATING DEGRADATION AND DURABILITY OF CONCRETE STRUCTURES AND ASSET MANAGEMENT SYSTEM MAKING USE OF SAME

CROSS REFERENCE TO RELATED APPLICATION

This application claims the benefit under 35 USC §119(e) of U.S. provisional patent application Ser. No. 61/771,475 filed on Mar. 1, 2013. The contents of the above-mentioned patent application are incorporated herein by reference.

FIELD OF THE INVENTION

The present invention relates generally to the field of management of concrete structures, such as roadways, bridges, parking structures, airport facilities, marine structures and the like, and more specifically to a computer implemented method, system and computer program product that allow estimating and predicting degradation and durability characteristics of such concrete structures. The approach presented may provide solutions to assist in planning maintenance activities in connection with concrete structures such as to prolong their useful life and better predict budgetary requirements over time for such maintenance activities. An approach suggested in the present document includes making use of a mechanistic approach that couples advanced reactive transport modeling, probabilistic analysis of input parameters and contribution from non-destructive testing field data (e.g. ground penetrating radar (GPR) measurements) in order to quantify the evolution over time of the severity of damage sustained by a specific concrete structure in specific environmental conditions. Optionally, the information quantifying the evolution over time of the severity of damage sustained by the specific concrete structure may be used in a life-cycle cost calculation process to optimize asset management, including the elaboration of a maintenance schedule, as it relates to the specific concrete structure.

BACKGROUND

Bridges and some roadways in modern countries throughout the world are frequently formed, in part, of concrete reinforced with steel. The supporting steel or other subsurface materials provide the strength needed for the overlying road surface to enable it to carry the massive weight loads of vehicles, trains and the like. Such roadways are found on soil or over the bridged rivers and canyons or simply on city and state streets.

The employment of metal reinforcement such as steel in the underlying concrete material supporting an overlying roadway provides support to the roadway. The metal reinforcing material such as reinforcing bar (a.k.a. rebar) or wire mesh, when engaged within concrete road surfaces or support surfaces, produces a structural material that exceeds the strength of either material if employed individually in the same sized structure. This hidden underlying support technology, provided by metal reinforcing material, has enabled roadways to withstand much higher weights for much longer periods than would be possible in an unreinforced roadway surface.

However in many industrialized countries, concrete infrastructure is aging rapidly. Roads, bridges, parking structures, airport facilities, and marine structures are impacted and show in many cases severe signs of degradation. One of the most important causes of the premature deterioration of concrete is the exposure to chlorides found in de-icing salts and seawater, which, upon penetration in the concrete cover, ultimately initiates the rebar corrosion process. Other types of degradation affect concrete structures, such as freezing and thawing damage, alkali-silica reaction (ASR), and exposure to acidic environments. In the United States only, it has been reported that more than two thirds of the six hundred thousand bridges are more than 25 years old, and thus likely to require serious maintenance. For additional information regarding this, the reader is invited to refer to FHWA—2010 Status of the Nation's Highways, Bridges, and Transit—Condition & Performance. Technical report, Report to congress, 2010—Exhibit 3-20 and Y. H. Huang, Adams T. M., and Pincheira J. A. "*Analysis of life-cycle maintenance strategies for concrete bridge decks*", Journal of Bridge Engineering, 9:250-258, 2004. The contents of the aforementioned document are incorporated herein by reference. According to various sources, between 34% of bridges older than 25 year old are structurally deficient or functionally obsolete. It has been estimated by some that it would cost approximately US $70-$90 billion to repair these structures, where about 20% of this cost would be directly due to corrosion. For additional information regarding this, the reader is invited to refer to Y. Liu et al., "*Modeling the time-to-corrosion cracking in chloride contaminated reinforced concrete structures*", ACI Materials Journal, 95:675-681, 1998 and T. J. Kirkpatrick et al. "*Impact of specification changes on chloride-induced corrosion service life of bridge decks*", Cement and Concrete Research, 32:1189-1197, 2002. The contents of the aforementioned documents are incorporated herein by reference.

For owners and managers, decaying reinforced concrete structures not only represent a major safety issue but also impose a growing financial burden at a time of unprecedented budget restrictions.

In light of the above, it is becoming increasingly important to find cost-effective solutions to improve the design of new concrete structures and optimize the maintenance of existing structures. The construction industry has clearly identified the urgent need for the accelerated development and introduction of innovative new technologies and processes to ensure the quality, durability, efficiency, and sustainability of infrastructure systems as well as support sound asset management and decision-making.

While the construction industry is clearly in need of life-cycle cost analysis tools that explicitly take into account the impact of material degradation, few suitable solutions are currently available. In particular, most available solutions for assessing the degradation of concrete structures and planning maintenance of such structures rely on the practical experience of structural engineers and on visual inspection. As such, the reliability of such solutions is highly dependent on the individual skills of those conducting the analysis and planning activities, which is inefficient and may not always result in concrete structures being properly managed and their safety being ensured.

Some numerical tools have been suggested for quantifying and predicting the long-term durability of concrete structures. Probabilistic approaches have also received attention recently. It is widely acknowledged that concrete, as a material, is inherently variable due to its heterogeneous composition of aggregates of multiple scales and casting techniques which introduce local variations in compositions of paste, water, and aggregate content. Furthermore, concrete structures are exposed to highly variable environmental conditions, which add to the need of using probabilistic concepts in the analysis.

However, conventional probabilistic methods used for quantifying and predicting the long-term durability of concrete structures generally fail to suitably consider the local variations in the properties of the concrete structures and fail to provide suitable mechanisms for taking into account local variations in degradation.

Against the background described above, there is a need in the industry to provide solutions for estimating and predicting degradation and durability characteristics of concrete structures that address at least some of the deficiencies of existing solutions and that can be used to assist in planning maintenance activities related to concrete structures.

SUMMARY

In accordance with a first aspect, the invention relates to a method for estimating degradation and durability characteristics of a concrete structure under test, the concrete structure under test being a reinforced concrete structure. The method is implemented by a system including at least one programmable processor and comprises receiving location-dependent information associated with the concrete structure under test and conveying structural information associated with different locations along the concrete structure under test. The location-dependent information is obtained by applying a non-destructive testing (NDT) process to the concrete structure under test. The method also comprises processing the location-dependent information associated with the concrete structure under test in combination with information conveying material properties associated with the concrete structure under test and information conveying estimated environmental conditions to which the concrete structure under test is subjected to derive concrete degradation simulation data. The derived concrete degradation simulation data information conveys estimated degradation and durability characteristics associated with at least some of the different locations along the concrete structure under test. The method also comprises releasing a signal causing the estimated degradation and durability characteristics of the concrete structure under test to be displayed on a display device in communication with the system.

In a specific example of implementation, the structural information conveyed by the location-dependent information may convey a state of the materials out of which the concrete structure under test is built. In specific practical implementations, the structural information associated with different locations along the concrete structure under test and conveyed by the location-dependent information may include, without being limited to:

location and surface area of delaminated material; and/or
location, depth, and length of fissures (cracks) in the material; and/or
estimated water content of the concrete material, and/or
location and quantity of reinforcing steel; and/or
location of current corrosion activity; and/or
location of voids; and/or
location and depth of existing repaired portions of the concrete structure under test; and/or
estimated thickness of the concrete material over the reinforcing steel at different locations along the concrete structure under test; and/or
information conveying a quality of the interface between the reinforcing steel rebar and the concrete materials.

In a non-limiting practical implementation, the NDT process applied to derive location-dependent information associated with the concrete structure under test includes using ground penetrating radar on the different locations along the concrete structure under test to derive the location-dependent information. However the person skilled in the art will appreciate that NDT processes other than those making use of ground penetrating radar may also be used in alternative implementations in order to derive location-dependent information associated with the concrete structure under test.

Advantageously, by making use of material properties and environmental properties of the concrete structure in combination with location-dependent information obtained by applying a non-destructive testing (NDT) process to the concrete structure under test, improved concrete degradation simulation information that takes into account local structural variations in the concrete structure may be obtained. This may allow, for example, taking into account variations in thickness of the covering material, variations in the specific depths of the rebar in the concrete structure, the location and extent of pre-existing repairs and the like. This may also allow taking into account local variations in degradation and the existence of local material defects on the concrete structure under test, such as fissures and cracks. This may also allow taking into account combined effects of local structural variations in the concrete structure and local variations of contaminant exposure, which may be caused by local drainage conditions for example, on the concrete structure under test.

In accordance with a specific implementation, the concrete structure under test is comprised in part of concrete material including cement, and possibly one or more of slag, fly ash and silica fume or any combination of these materials.

In accordance with a specific implementation, the concrete degradation simulation data may convey current estimated degradation and durability characteristics associated with the different locations along the concrete structure under test. Alternatively, or in addition, the concrete degradation simulation data may convey an evolution over a time period of the estimated degradation and durability characteristics associated with the different locations along the concrete structure under test. The duration of the time period can vary from one implementation to the other and multiple time periods may be made available to a user. Practical system will generally make use of time periods that corresponds to at least the projected service life of the structure (for example 10, 25, 50, 100 years).

The time period for the simulation may be established by default (for example it may be pre-determined by computer program instructions executed by the system) or may be specified by a user of the system implementing the method, for example by providing a user operable control in communication with the system to allow the user to specify a time period for which degradation simulation is desired. In such implementation, the method further comprises receiving from the user operable control (for example touch sensitive screen, keyboard, mouse, voice input, user created data file or the like) information conveying the time period for which the degradation simulation associated with the concrete structure under test is desired.

In accordance with a specific implementation, at least a portion of the information conveying material properties associated with the concrete structure is derived based on analysis applied to a set of cores extracted from the concrete structure under test.

In accordance with a specific implementation, the information conveying estimated environmental conditions to which the concrete structure under test is subjected conveys temperature information and/or information related to humidity levels and/or information related to exposure to aggressive agents.

Specific practical implementations of the above-described method may be used for estimating degradation and durability characteristics of different types of reinforced concrete structures, such as for example bridges, ports and roadways, and may be configured to apply to either one or both newly constructed concrete structures and existing concrete structures.

In accordance with a specific example, the method couples the use of an advance reactive transport model in the context of a probabilistic algorithm based on point estimators with data obtained from non-destructive testing such as ground penetrating radar. In some implementations, the use of an advance reactive transport model in the context of a probabilistic algorithm based on point estimators may have the advantage of limiting the number of simulations required to arrive to a reliable estimation of the degradation level of a concrete structure. In some implementation, the incorporation of data obtained from non-destructive testing, such as ground penetrating radar, may allow accounting for spatial variations in concrete cover quality, and the localization of critical areas of either one or both current and future degradation.

In accordance with another aspect, the invention relates to a system for estimating degradation and durability characteristics of a concrete structure under test, the concrete structure under test being a reinforced concrete structure. The system comprises a set of inputs for receiving information associated with the concrete structure under test. The system also comprises a concrete degradation simulation unit for processing the information received at the set of inputs for estimating degradation and durability characteristics of the concrete structure under test in accordance with the above described method. The system also comprises a display device for displaying information conveying degradation and durability characteristics of the concrete structure under test based on results derived by the concrete degradation simulation unit.

In accordance with another aspect, the invention relates to a computer program product, tangibly stored on one or more tangible computer readable storage media, for estimating degradation and durability characteristics of reinforced concrete structures. The computer program product comprises instructions that, when executed, cause a programmable system including at least one programmable processor to perform the above described method.

In accordance with another aspect, the present invention relates to an asset management system that makes use of a method for estimating degradation and durability characteristics of concrete structures of the type described above.

These and other aspects and features of the present invention will now become apparent to those of ordinary skill in the art upon review of the following description of specific embodiments of the invention in conjunction with the accompanying drawings.

BRIEF DESCRIPTION OF THE DRAWINGS

A detailed description of the embodiments of the present invention is provided herein below, by way of example only, with reference to the accompanying drawings, in which.

Figure 1:
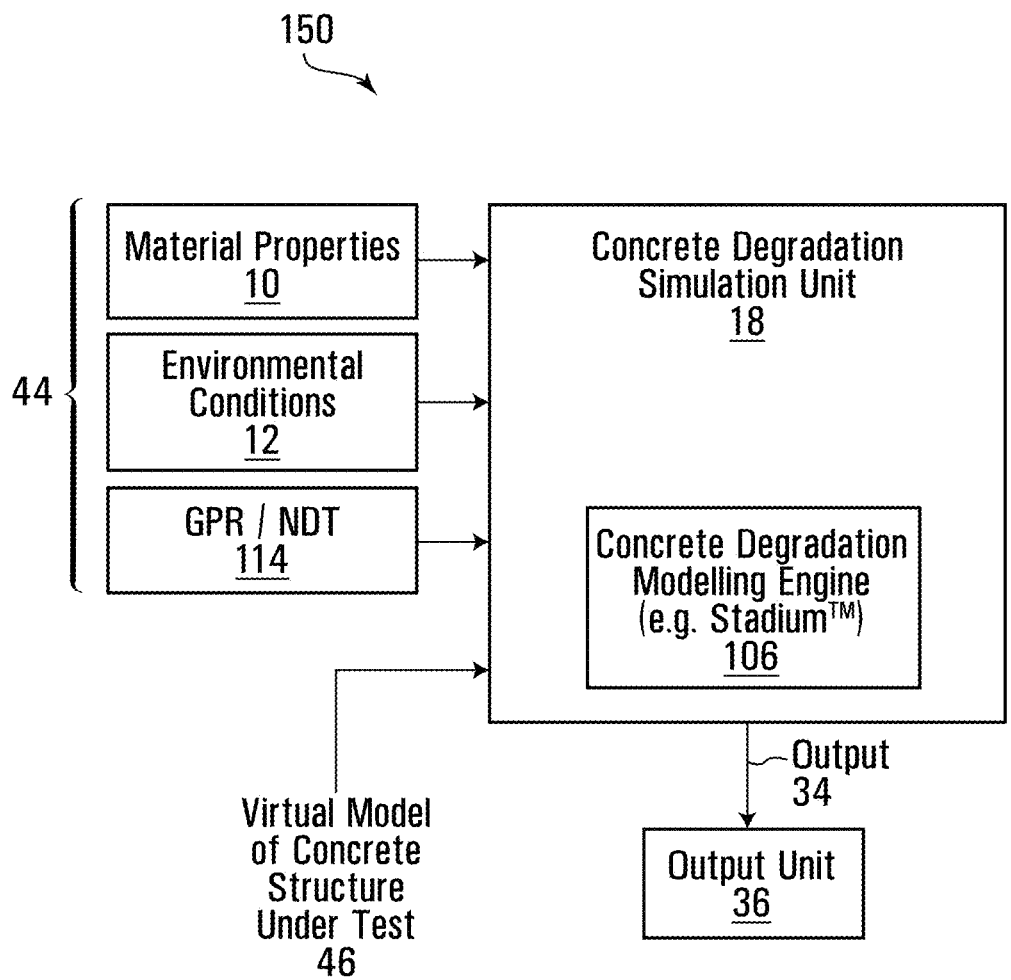
FIG. 1 shows a block diagram of a system for estimating degradation and durability characteristics of a concrete structure under test in accordance with a specific example of implementation of the invention.

In the drawings, the embodiments of the invention are illustrated by way of examples. It is to be expressly understood that the description and drawings are only for the purpose of illustration and are an aid for understanding. They are not intended to be a definition of the limits of the invention.

DETAILED DESCRIPTION

FIG. 1 shows a functional block diagram of a system 150 for estimating and predicting degradation and durability characteristics of concrete structures under test in accordance with a specific example of implementation of the invention. It is to be appreciated that some practical systems making use of the concepts presented in the present application may include modules other than the ones depicted in a FIG. 1. Such modules have been omitted from the present application for the purpose of simplifying the description and in order to facilitate the understanding of the concepts described. Some examples of variants of the system of FIG. 1 will be described later on in the present application, for example with reference to FIG. 13. It is to be appreciated that the examples described in the present application have been described for the purpose of illustration only and that many other variants are possible and will become apparent to the person skilled in the art in light of the present description.

As depicted in FIG. 1, the system 150 includes a set of inputs 44 for receiving information associated with a specific concrete structure under test, a concrete degradation simulation unit 18 for processing the information received at the set of inputs 44 to derive concrete degradation simulation data conveying estimated degradation and durability characteristics associated with the concrete structure under test and an output unit 36 in communication with the concrete degradation simulation unit 18 for receiving the concrete degradation simulation data and for displaying information based in such data.

The set of inputs 44 is for receiving information associated with the concrete structure under test and based on which a simulation of concrete degradation will be performed by unit 18. Such information includes information intrinsic to the concrete structure, such material and structural properties of the concrete structure, as well as information external to the concrete structure, such as information pertaining to environmental conditions. In the specific example depicted, the set inputs 44 include:

a) first input 10 for receiving information conveying material properties associated with the concrete structures under test;

b) second input 12 for receiving information conveying estimated environmental conditions to which the concrete structure under test is subjected; and c) third input 114 for receiving location-dependent information associated with the concrete structure under test and conveying structural information associated with different locations along the concrete structure under test. The location-dependent information may be obtained by applying a non-destructive testing (NDT) process, which may include ground penetrating radar (GPR), to the concrete structure under test.

Figure 2:
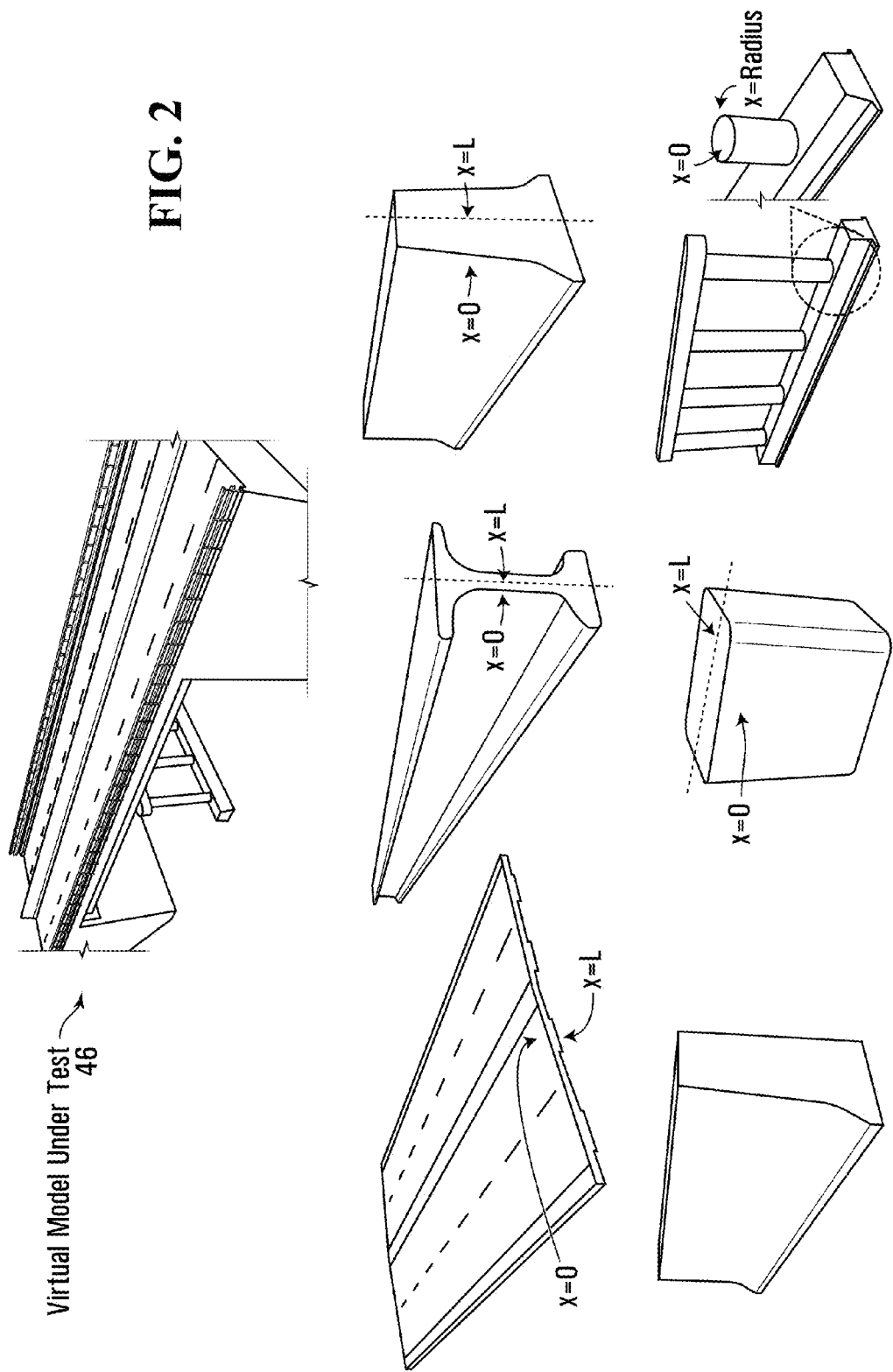
FIG. 2 is a graphical illustration of a virtual model of a concrete structure under test (in this example a bridge) that may be used by the system depicted in FIG. 1 in accordance with a specific example of implementation of the invention.

In the example depicted, the system 150 also makes use of a virtual model 46 of the concrete structure under test. In a specific example, the virtual model 46 of the structure under test is a mathematical representation of the structure, which may provide, amongst other, material, geometrical and structure information related to the concrete structure (length, width, thickness, location of rebar etc. . . . ). FIG. 2 of the drawings shows graphical representation of a virtual model 46 of a concrete structure under test, which in this example is a bridge. Any suitable tool may be used for generating the virtual model 46 of the structure under test. Several such tools are known in the art of concrete structure design and the particular features of such tools are beyond the scope of the present application and thus will not be described further here. It is to be appreciated that while FIG. 2 shows components of a virtual model of a bridge that has sufficient detail to generate a full three-dimensional (3D) rendering of the bridge and its component, alternative implementations may make use of virtual models with fewer details while providing basic geometrical information and allowing for spatial positioning of parts of the concrete structure under test.

The concrete degradation simulation unit 18 makes use of a concrete degradation modeling engine 106 to process the information received at the set of inputs 44 and the virtual model 46 in order to derive concrete degradation simulation data conveying estimated degradation and durability characteristics associated with different locations along the concrete structure under test. A non-limiting example of a concrete degradation modeling engine 106 that may be used is a service-life prediction software commercialized by SIMCO Technologies Inc. under the name STADIUM®. It is to be appreciated that other suitable concrete degradation modeling engines 106 may be used in alternative implementations. In addition, it is to be appreciated that, while the concrete degradation modeling engine 106 has been shown to be a component within the concrete degradation simulation unit 18 in the embodiment depicted in FIG. 1, the concrete degradation modeling engine 106 may be implemented by a system separate from the concrete degradation simulation unit 18 and which communicates with the concrete degradation simulation unit 18 over a computer network, for example.

The concrete degradation simulation data, generated by the concrete degradation simulation unit 18 and released at output 34, may convey current estimated degradation and durability characteristics associated with different locations along the concrete structure under test. Alternatively, or in addition, the concrete degradation simulation data may convey estimated degradation and durability characteristics associated with different locations along the concrete structure under test over future time periods. The duration of the time period can vary. Practical system will generally make use of time periods that correspond to at least the projected service life of the structure (for example 10, 25, 50 and 100 years). The specific manner in which the concrete degradation simulation unit 18 uses the degradation modeling engine 106 to derive the simulation data may vary. Specific examples of approaches will be described later on in the present specification. The concrete degradation simulation data derived by the concrete degradation simulation unit 18 is propagated to the output unit 36 by releasing the data at output 34.

Figure 9:
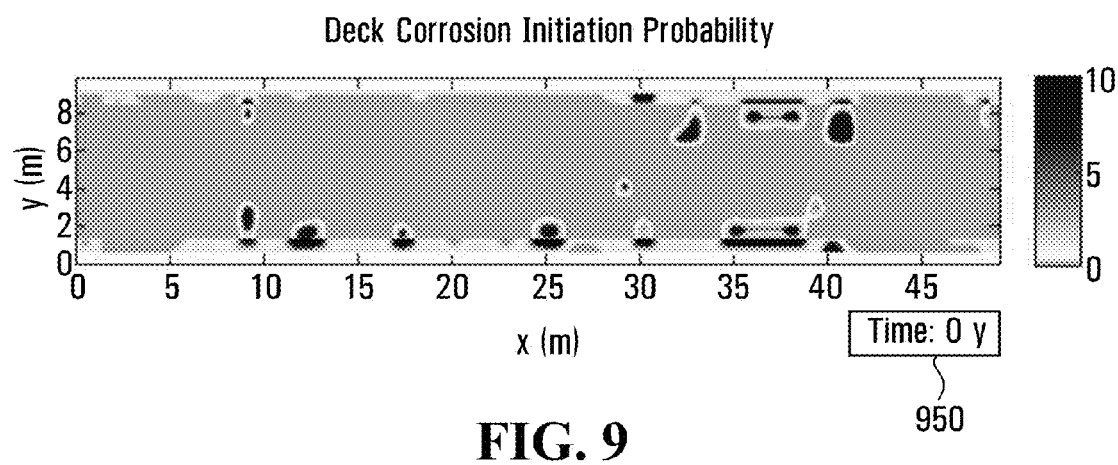
FIG. 9 is a graphical representation of current estimated degradation and durability characteristics of a concrete structure under test in accordance with a specific example of implementation of the invention. In this example, the current estimated degradation and durability characteristics convey a probability of corrosion initiation at different locations on the surface.
Figure 10:
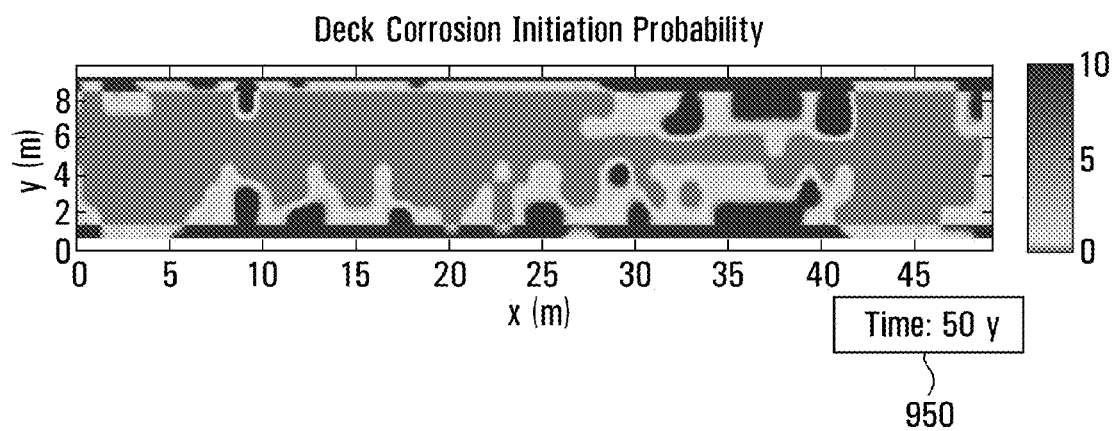
FIG. 10 is a graphical representation of estimated degradation and durability characteristics of a concrete structure under test after a time delay of 50 years has elapsed in accordance with a specific example of implementation of the invention. As was the case for FIG. 9, in this example, the estimated degradation and durability characteristics convey a probability of corrosion initiation at different locations on the surface.

In specific implementations, the output unit 36 may include a display device, such as a display screen, for conveying a visual representation of the derived concrete degradation simulation data. In such implementation, the concrete degradation simulation unit 18 may be programmed with suitable software code for rendering a display image for graphically conveying the derived concrete degradation simulation data to a user. The specific manner in which the derived concrete degradation simulation data may be displayed may vary significantly from one implementation to the other and may depend, amongst other, on user preferences, on the type of information that is of interest to the user and on the type of concrete structure under test (for example whether it is a bridge, a road, a parking structure, etc. . . . ). Non-limiting examples of manners in which information may be displayed will be described later on in the present application. Such examples include, but are not limited to:

- A graph showing a top-down view of the reinforced concrete structure under test with color-coded indications showing the amount of degradation associated with different areas/locations of the structure. FIGS. 9 and 10 are non-limiting examples of such displayed information. More specifically, FIG. 9 is a graphical representation of current (as indicated in box 950—time: 0 years) estimated degradation and durability characteristics of a concrete structure under test in accordance with a specific example of implementation of the invention. FIG. 10 is similar to FIG. 9 but shows estimated degradation and durability characteristics of a concrete structure under test after a time delay of 50 years have elapsed (as indicated in box 950—time: 50 years). In both these display examples, the displayed estimated degradation and durability characteristics convey a probability of corrosion initiation at different locations on the surface of the concrete structure. FIGS. 9 and 10 will be described later on in the present document.

Figure 11:
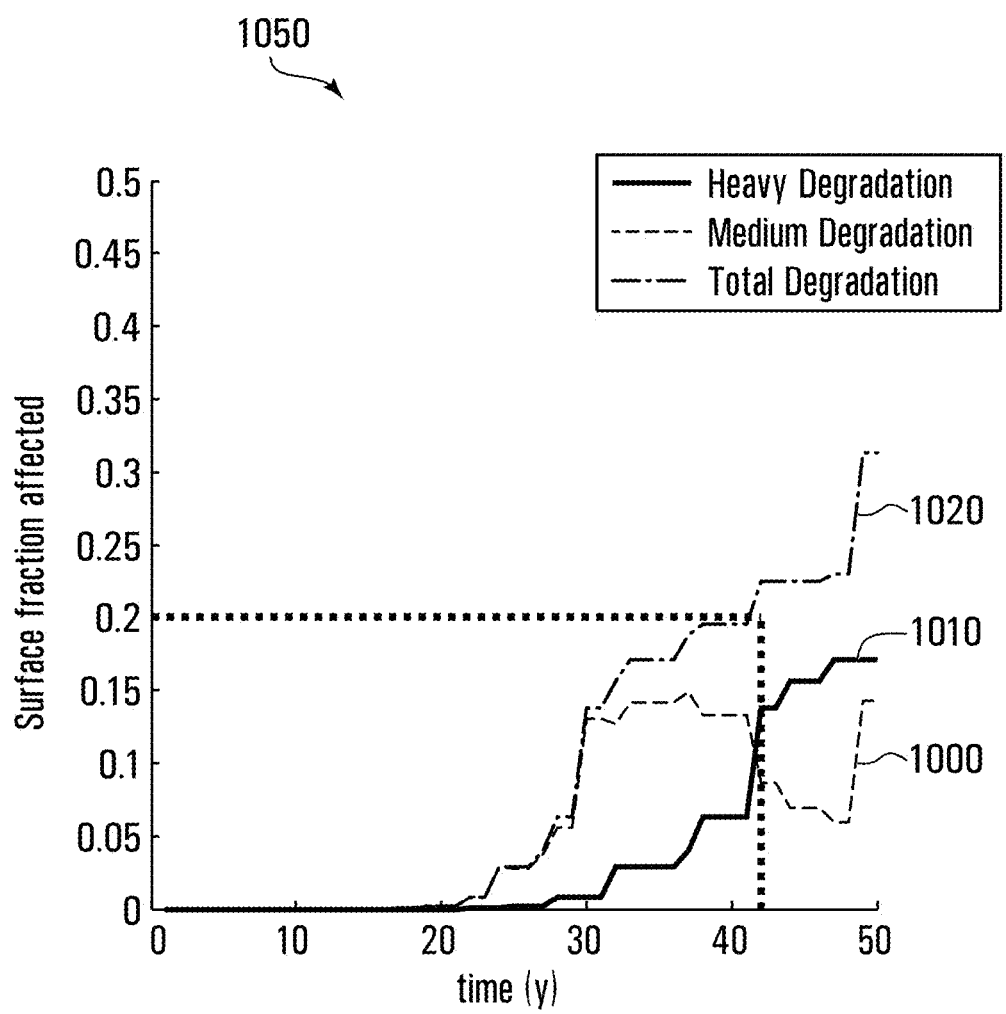
FIG. 11 is a graphical representation of estimated degradation and durability characteristics of a concrete structure under test in accordance with another specific example of implementation of the invention. In this example, the estimated degradation and durability characteristics convey what portion (or fraction) of the structure would likely be affected at a given degradation level after different time delays and accounting for different levels of degradation.

- A (line-plot) graph showing what fraction of the concrete structure under test would likely be affected by a given level of a degradation mechanism over a period of time. FIG. 11 is a non-limiting example of such displayed information. More specifically, FIG. 11 is a graphical representation of estimated degradation and durability characteristics of a concrete structure under test in accordance with another specific example of implementation of the invention. In this example, the estimated degradation and durability characteristics convey what portion (or fraction) of the structure would likely be affected at a given degradation level after different time delays and accounting for different levels of degradation, in this case heavy degradation and medium degradation. FIG. 11 will be described later on in the present document.

Figure 8:
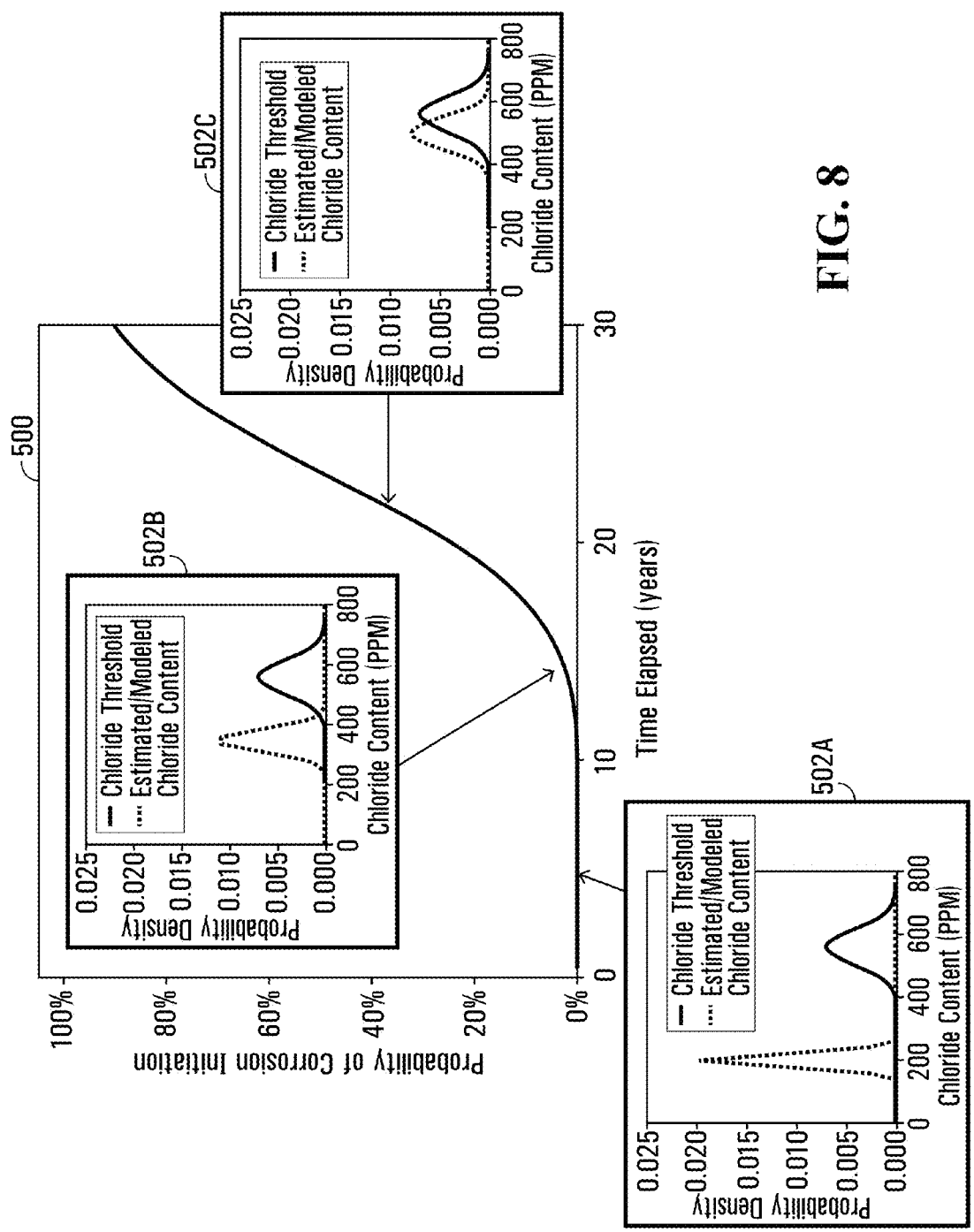
FIG. 8 show a graph depicting a sample degradation curve, which may be derived by a probabilistic layer module part of the concrete degradation simulation unit shown in FIG. 6, wherein the sample degradation curve conveys likelihoods of initiation of corrosion of rebar caused by chloride ingress in accordance with a specific example of implementation of the invention.

- A line-plot graph conveying probabilities of degradation at a specific location of the concrete structure under test over a period of time. FIG. 8 is a non-limiting example of such a line-plot graph. More specifically, FIG. 8 show a graph 500 depicting a sample degradation curve conveys likelihoods of initiation of corrosion of rebar caused by chloride ingress in accordance with a specific example of implementation of the invention. FIG. 8 will be described later on in the present document.

The output unit 36 may include non-transient computer readable storage media for storing the concrete degradation simulation data derived by the concrete degradation simulation unit 18 and released at output 34. The concrete degradation simulation data may be stored on such a computer readable storage medium in any suitable format for later access by suitably programmed systems for processing and interpreting such data and/or for using such data in connection with tools for assisting in planning maintenance activities related to concrete structures. In yet another alternative implementation the output unit 36 may include a printing device for generating a printed representation of the derived concrete degradation simulation data released at output 34. In such implementations, the concrete degradation simulation unit 18 may be programmed with suitable code for controlling the printing device.

Set of Inputs 44

Specific examples of the type of information received by the set of inputs 44 based on which simulation of concrete degradation is performed by unit 18 will now be described.

Estimated Environmental Conditions (Input 12)

In specific examples of implementation, the information received at input 12 conveying estimated environmental conditions to which the concrete structure under test is subjected may include (for example but not limited to):

- Temperature information surrounding the concrete structure under test. This may include, in some cases, yearly cycles in temperature conveying temperature fluctuations occurring over a one-year period;
- Information related to humidity levels. This may include, in some cases, average relative humidity levels over a one-year period;
- Information conveying levels of exposure to aggressive agents (also referred to as "contaminant exposure levels") by the concrete structure under test, such as de-icing salts and seawater. This may include, in some cases, estimated past exposure levels to such agents over a one-year period. Alternatively, or in addition, the information conveying contaminant exposure levels by the concrete structure under test may be derived by the exposure condition determination module 102 (shown in FIG. 6), which will be described in greater detail later on in the present document.

Figure 3:
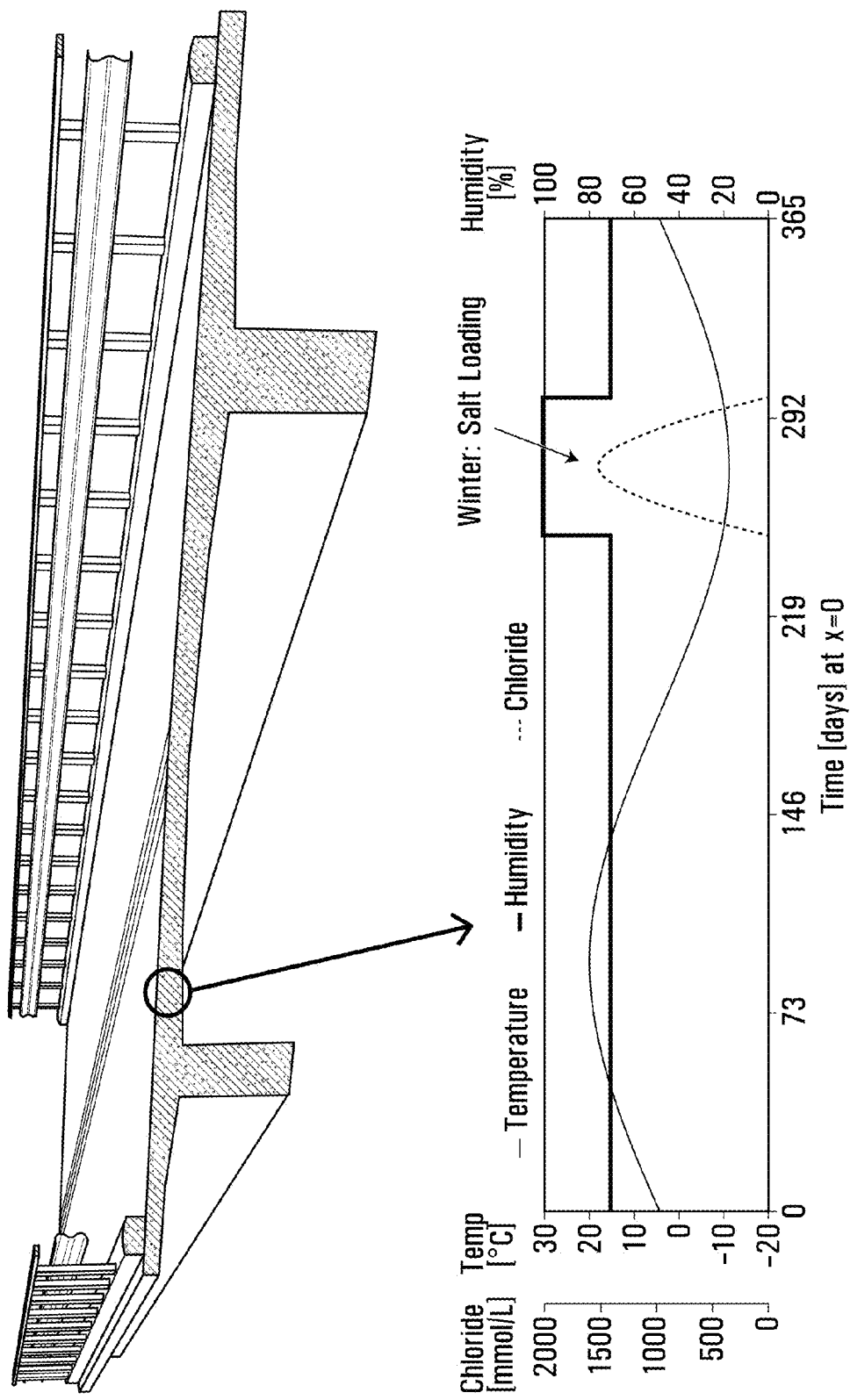
FIG. 3 is a graphical illustration of information conveying estimated environmental conditions to which a concrete structure under test is subjected that may be received at an input of the system depicted in FIG. 1 in accordance with a specific example of implementation of the invention.

FIG. 3 of the drawings illustrates graphically the information conveying estimated environmental conditions to which the concrete structure under test is subjected that may be received at input 12. In practical systems, the information conveying estimated environmental conditions would be based on historical data and past environmental conditions would be used by the concrete degradation simulation unit 18 to estimate future environmental conditions to which the concrete structure under test will be exposed and for which simulations will be performed. It is to be appreciated that while specific examples of information conveying estimated environmental conditions received at input 12 have been described above, it is to be expressly understood that alternative embodiments of the invention may include additional information and/or may omit certain types of information.

Material Properties (Input 10)

In a specific implementation, the information conveying material properties received at input 10 is used to provide information describing the material composition of the concrete used in the concrete structure under test. In specific examples of implementation, the information conveying material properties associated with the concrete structure under test received at input 10 may include (for example but not limited to):

Binder physical properties, such as density and fineness,
Binder chemical properties, such as mineral phases,
Concrete aggregate information, such as quantity and density,
Concrete mix properties, such as water-to-binder ratio,
Concrete mix transport properties, such as volume of permeable voids, ionic diffusion coefficients, and water transport properties.

In practical implementations of the system 150, a portion of the information conveying material properties received at input 10 may be derived by analysing a set of cores extracted from the specific concrete structure under test. Such an approach typically involves taking one or more sample cores at different locations on the concrete structure under test in order to get a sampling of the material over the surface of the structure and then applying various tests to the sampled cores. Optionally, the material properties received at input 10 may be associated to specific locations along the concrete structure under test by mapping such properties to locations on the virtual model 46 of the concrete structure. Many different suitable types of analysis may be performed on the sample cores in order to characterize the concrete material along the surface of the concrete structure in order to derive characteristic of the type described above. Any suitable approach for analysing sample cores in order to derive characteristics of the concrete material along the surface of the concrete structure may be used in specific examples of implementation. Several such approaches are known in the art of concrete structure analysis and the specifics of such approaches are beyond the scope of the present application and thus will not be described further here.

Location-Dependent Information—(for Example GPR/NDT Information) (Input 114)

In specific examples of implementation, the location-dependent information conveying structural information associated with different locations along the concrete structure under test received at input 114 may include information conveying one or more of the following (for example but not limited to):

Location and surface area of delaminated material, and/or
Location, depth, and length of fissures (cracks) in the material, and/or
Estimated water content of the concrete material, and/or
Location (including depth under the concrete cover) and quantity of reinforcing steel rebar, and/or
Quality of the interface between the reinforcing steel rebar and the concrete materials, and/or
Location of current corrosion activity, if it exists, and/or
Location of voids, and/or
Depth of existing repairs, and/or
Estimated thickness of the concrete material over the reinforcing steel at different locations along the concrete structure under test.

In practical implementations of the system 150, a portion of the location-dependent information received at input 114 may be obtained by applying a non-destructive testing (NDT) process, such as a process using ground penetrating radar (GPR), to the concrete structure under test. In a specific implementation, an information gathering system using ground penetrating radar (GPR) mounted on a vehicle travelling along the concrete structure under test is used to generate data suitable for deriving at least a portion of the location-dependent information of the type described above. Any suitable approach for deriving location-dependent information conveying properties associated with a concrete structure based on radar generated data may be used. Several such approaches are known in the art of concrete structure analysis and the specifics of such approaches are beyond the scope of the present application and thus will not be described further here. It is also to be appreciated that while ground penetrating radar (GPR) has been mentioned as a specific example of non-destructive testing (NDT), other methods for conducting non-destructive testing (NDT) on concrete structures to derive location-dependent information may be used. Examples of such alternate methods may include, for example, ultrasound-based methods, impact-based methods, induction-based methods, electrical potential based methods, camera-imaging based methods, and the like. For some examples of methods and devices useful for generating location-dependent information of the type mentioned above, the reader is invited to refer to the documents listing in Appendix I of the present document, the contents of which are incorporated herein by reference.

In a specific practical implementation, the location-dependent information received at input 114 may include GPR survey data obtained of the concrete cover over the steel rebar of the concrete structure under test in order to derive information for modeling chloride-induced corrosion of the steel rebar. Amongst other, the GPR survey data conveys the mean and variability of the depth of the steel rebar for which the concrete degradation should be modeled with the concrete degradation modeling engine 106 (such as for example the STADIUM® tool).

For the purpose of illustration, additional details regarding a manner in which GPR survey data may be collected and used in the context of the system depicted in FIG. 1 will now be described.

GPR Survey Data

As described above, in a specific practical implementation, the location-dependent information received at input 114 may include GPR survey data. The GPR survey data received may include a series of measurement points localized on the surface of the concrete structure under test. The measurement points may be acquired automatically by an automated system, wherein the automated system acquires the localization and measurement of depth of the concrete cover using a computerized system. Measurement depth of the concrete cover may also be provided by hand-held systems for which the location is recorded by the operator.

The measurement points convey the estimated thickness (measurement depth) of the concrete material over the reinforcing steel at different locations along the concrete structure under test. In the specific example of chloride-induced corrosion of steel rebar within the concrete material, the depth of concrete cover provides a protective barrier against chlorides. The thickness of concrete through which chlorides must travel in order to act on and initiate corrosion of reinforcing steel is therefore useful to model the degradation of the concrete structure.

Interpolation of Data Points

Figure 4:
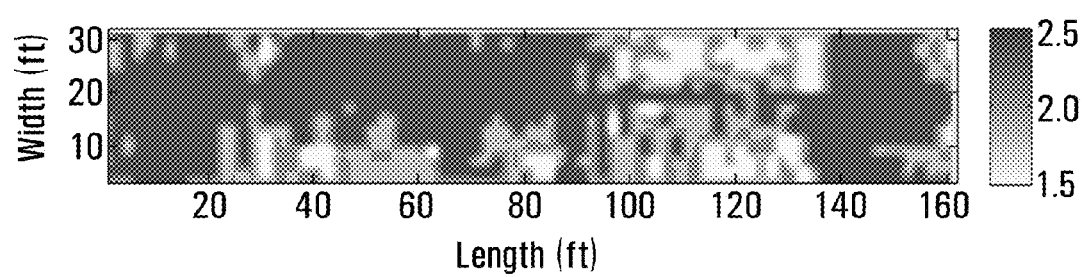
FIG. 4 is a graphical representation of NDT data in the form of interpolated GPR survey data over a portion of a surface of a concrete structure under test. The graph conveys the thickness of the concrete material over the reinforcing steel at different locations along the surface of the concrete structure under test.

The different GPR survey data points obtained are associated to respective locations over the surface of the structure. In order to derive a representation of the depth of concrete cover along different points (locations) of the structure, the data points may be interpolated using (for example) a uniformly-spaced matrix, for example using cubic interpolation. Using such an approach, the surface of the concrete structure may be divided into sub-surfaces that have equal areas. The exact area may depend on the level of precision of the GPR survey data and the total surface area. In a practical case, each subsurface may represent an area of 100 to 900 $cm^2$ (approx. 16 to 144 $in^2$), wherein each subsurface is assumed to have one rebar depth. FIG. 4 shows graphical representation of interpolated GPR survey data over a portion of a surface of a concrete structure (which in this example is a portion of a concrete bridge deck). The graphical representation conveys the thickness of the concrete material over the reinforcing steel at different locations. Darker areas on the graph shown in FIG. 4 are associated to locations along the concrete structure that have a thicker concrete cover while lighter areas on the graph are associated to locations along the concrete structure that have a thinner concrete cover.

Now that the inputs 44 shown in FIG. 1 have been described, the functionality implemented by the concrete degradation unit 18 in order to derive concrete degradation simulation data for output 34 will now be described in the sections that follow.

Concrete Degradation Simulation Unit 18

Figure 5:
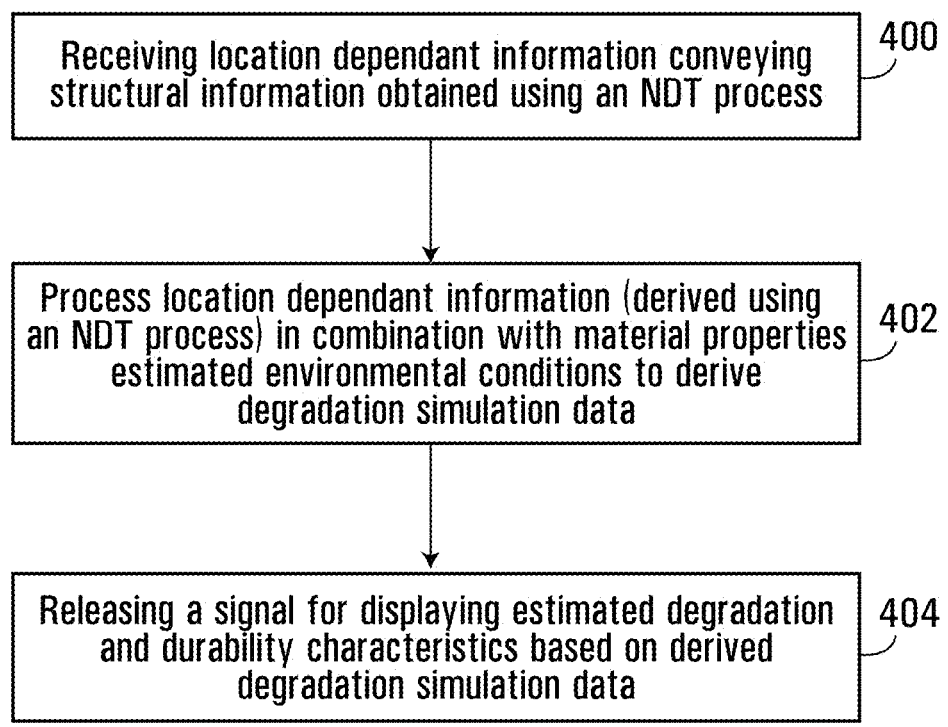
FIG. 5 is a flow diagram of a process implemented by the system for estimating degradation and durability characteristics of a concrete structure under test shown in FIG. 1 in accordance with a specific example of implementation of the invention.

FIG. 5 is a flow diagram of a process implemented by the system 150 for estimating degradation and durability characteristics of a concrete structure under test shown in FIG. 1 in accordance with a specific example of implementation of the invention.

As shown at step 400, location-dependent information associated with the concrete structure under test and conveying structural information associated with different locations along the concrete structure under test is received by the concrete degradation simulation unit 18 at input 114 (both shown in FIG. 1). The location-dependent information received was obtained at least in part by applying a non-destructive testing (NDT) process. In a specific example, the non-destructive testing (NDT) process includes the use of ground penetrating radar on the different locations along the concrete structure under test to derive information conveying measurements of depth of the concrete cover over the surface.

At step 402, the concrete degradation simulation unit 18 (shown in FIG. 1) processes the location-dependent information received at input 114 in combination with:

i) information conveying material properties associated with the concrete structure under test; and ii) information conveying estimated environmental conditions to which the concrete structure under test is subjected.

In the specific example shown, at least part of the information conveying material properties is received at input 10 and at least part of the information conveying estimated environmental conditions to which the concrete structure under test is subjected is received at input 12. The processing performed by the concrete degradation simulation unit 18 at step 402 is for deriving concrete degradation simulation data conveying estimated degradation and durability characteristics associated with different locations along the concrete structure under test. In specific implementations, the derived concrete degradation simulation data may consider one or more types of concrete degradation mechanisms. Examples of types of concrete degradation mechanisms that may be simulated include, without being limited to: chloride ingress, carbonation of concrete, freezing/thawing delamination, and/or a combination thereof.

At step 404, the concrete degradation simulation unit 18 (shown in FIG. 1) releases a signal at output 34 for causing the estimated degradation and durability characteristics of the concrete structure under test derived at step 402 to be conveyed by output unit 36, for example by displaying information on a display device.

A specific example of implementation of the concrete degradation simulation unit 18 depicted in FIG. 1 will now be described with reference to FIG. 6. It is to be appreciated that the specific example shown in FIG. 6 is only one of many possible manners in which the functionality of the concrete degradation simulation unit 18 may be implemented and is being described here for the purpose of illustration only and to facilitate the reader's understanding of the concepts set forth in the present document.

Figure 6:
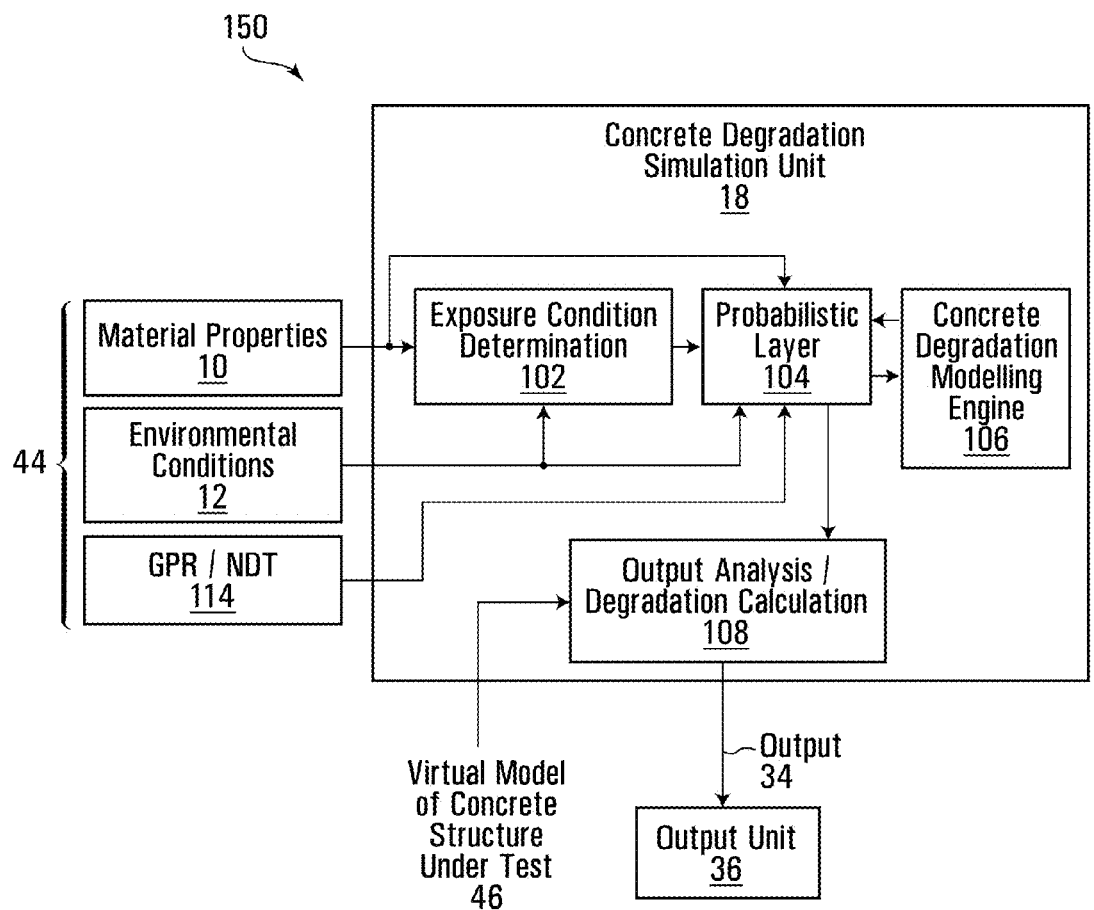
FIG. 6 is a block diagram of the system shown in FIG. 1 for estimating degradation and durability characteristics of a concrete structure under test showing in greater detail components of a concrete degradation simulation unit in accordance with a specific example of implementation of the invention.

In the embodiment shown in FIG. 6, the concrete degradation simulation unit 18 includes an exposure condition determination module 102, a probabilistic layer module 104 and an output analysis/degradation calculation unit 108. The embodiment depicted in FIG. 6 also includes the concrete degradation modeling engine 106 (also depicted in FIG. 1). It is to be noted that in alternative examples of implementation, the concrete degradation modeling engine 106 may be a component separate from the concrete degradation simulation unit 18.

The exposure condition determination module 102 processes the information conveying material properties received at input 10 and the information received at input 12 conveying estimated environmental conditions to which the concrete structure under test is subjected in order to estimate the most likely contaminant exposure levels (for example de-icing salts, seawater and the like) to which the concrete structure may be subjected. In a specific example, module 102 calculates past salt loading levels to reproduce current contaminant levels in the structure at specific points. Different suitable approaches for deriving contaminant exposure levels may be used in specific examples of implementation. A non-limiting example of such an approach will be described later on in the present document for the purpose of illustration.

The probabilistic layer module 104 processes the location-dependent information conveying structural information received at input 114 as well as the material properties (received at input 10), environmental condition information (received at input 12) and (optionally) contaminant exposure levels derived by exposure condition determination module 102 in order to derive degradation curves associated with different locations along the surface of the concrete structure. In a specific implementation, the probabilistic layer module 104 derives stochastic simulations parameters which are then provided to the concrete degradation modeling engine 106 for deriving degradation characteristics at specific locations of the structure by simulating concrete degradation results using such parameters. In performing this processing, in a specific example, the probabilistic layer module 104 makes multiple calls to the concrete degradation modeling engine 106 to iteratively derive concrete degradation simulation results for multiple specific sets of parameters. In specific implementations, the concrete degradation simulations results derived by the probabilistic layer module 104 (from the concrete degradation modeling engine 106) may consider one or more types of concrete degradation mechanisms. Examples of types of concrete degradation mechanisms that may be simulation include, without being limited to: chloride ingress, carbonation of concrete and/or a combination thereof. In practical non-limiting implementations, chloride ingress has been used to provide an indication of degradation of the concrete structure in light of its impact on the onset of corrosion of rebar.

The analysis/degradation calculation unit 108 processes the simulated concrete degradation results for multiple specific sets of parameters derived by the probabilistic layer module 104 in order to derive information conveying current and future levels of degradation for specific locations along the surface of the concrete structure under test. In specific implementations, the levels of degradation may be associated with a specific type of degradation mechanism simulated by the probabilistic layer module 104. Optionally, the analysis/degradation calculation unit 108 can combine the simulated concrete degradation results associated with different types of degradation mechanisms acting on a same resistance system of the concrete structure under test. For example, simulation results for concrete carbonation and chloride ingress which have well-known symbiotic effects on corrosion degradation of rebar in concrete may be combined using any suitable well-known approach in order to derive compound degradation simulation results conveying a probability of degradation of concrete caused by the combined effect of these two types of degradation mechanisms. The analysis/degradation calculation unit 108 releases concrete degradation simulation data that may convey current estimated degradation and durability characteristics associated with the different locations along the concrete structure under test. Alternatively, or in addition, the concrete degradation simulation data derived by the analysis/degradation calculation unit 108 may convey estimated degradation and durability characteristics over future time periods. The duration of the time period can vary. Practical system will generally make use of time periods that corresponds to at least the projected service life of the structure (for example 10, 25, 50, 100 years or longer).

The respective functionality implemented by each of the aforementioned modules 102, 104, 106 and 108 of the concrete degradation simulation unit 18, according to an embodiment of the invention, will be described in greater detail below.

Exposure Condition Determination—Module 102

As described above, the exposure condition determination module 102 processes the information conveying material properties received at input 10 and the information received at input 12 conveying estimated environmental conditions to which the concrete structure under test is subjected in order to derive exposure parameters conveying contaminant exposure levels for use in simulating exposure conditions for the concrete structure under test.

In a specific example of implementation in which one of the concrete degradation mechanisms to be simulated is chloride ingress, exposure parameters conveying contaminant exposure levels are derived by determining the chloride concentration at the exposed surface, which is determined from the material properties received at input 10. Any suitable approach for deriving exposure parameters known in the art may be used. A standardized method the determination of this chloride concentration at the exposed surface is known in the art and available as part of the ASTM 1556-04 standard.

In a specific practical implementation, a portion of the information conveying exposure conditions may be derived by performing an analysis of material properties derived from a set of cores extracted from different locations on the concrete structure under test. In such cases, the contaminant exposure levels derived by the exposure condition determination module 102 may be associated to specific locations (from which the cores were extracted) along the concrete structure under test.

In this context, distinct exposure conditions that best reproduce the measured contamination level (which are conveyed by distinct exposure parameters) may be associated with different locations on the concrete structure under test. In particular, the exposure parameters may be derived by applying a process of the type described above for different locations on the concrete structure under test for which material properties are provided at input 10 (which would typically correspond to the material properties of the cores taken from the structure).

Figure 7:
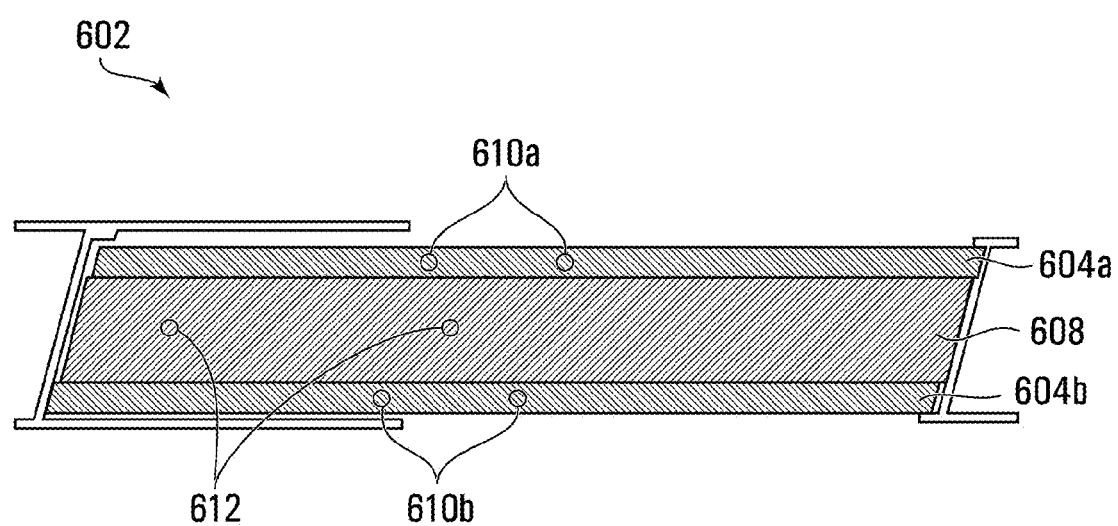
FIG. 7 shows a graphical representation of an exposure conditions map for a specific concrete structure under test, which in this non-limiting specific example is a concrete bridge deck.

Optionally, after determining exposure conditions (and associated exposure parameters) that likely to have produced measured contamination levels (as conveyed by material properties received at input 10), an exposure map can be produced. This exposure map may take into account the location of the cores from which the measured contamination levels were obtained by providing different exposure parameters for different locations along the concrete structure based on these measurements. Exposure parameters associated with locations along the concrete structure between the cores may be derived by using suitable interpolation techniques. In a specific implementation, a linear interpolation approach is used for deriving exposure parameters associated with locations along the concrete structure between the cores. It is to be appreciated that the greater the number of cores, the more precise the interpolation results may be obtained. 7 is a graphical representation of an exposure conditions map 602 for a specific concrete structure under test, which in this specific example is a concrete bridge deck. In this example, the longitudinal sides 604a 604b of the concrete deck would be associated with a first set of exposure parameters derived using material properties of one or more cores (for example 610a 610b) taken from at least one of these portions of the bridge deck. Conversely, the center portion 608 of the concrete deck would be associated with a second set of exposure parameters derived using material properties of one or more cores (for example 612) taken from that portion of the bridge deck. In this specific example, the exposure level of the longitudinal sides 604a 604b of the concrete deck may be more severe than the exposure level in the center portion 608, which may be due to differential drainage conditions. While the example depicted in FIG. 7 shows an exposure map with essentially three distinct sections (namely the center section and the longitudinal sections), it is noted that alternative implementation may derive exposure maps with any suitable number of distinct sections.

Probabilistic Layer—Module 104

As will be appreciated by persons skilled in the art, concrete production involves variation in the composition of the material. Furthermore, concrete structures are exposed to highly variable environmental conditions. In order to account for such variability, in a specific implementation, a probabilistic approach to concrete degradation simulation is implemented by the probabilistic layer module 104.

More specifically, a suggested approach to modeling degradation of concrete in aggressive environments is based upon a probabilistic approach, which takes into account both systemic uncertainties from material production and modeling uncertainty when modeling/simulating material degradation.

As described above, the probabilistic layer module 104 is configured to process the location-dependent information, conveying amongst other structural information associated with the concrete structure under test (received at input 114) as well that the material properties (received at input 10), environmental condition information (received at input 12) and (optionally) the information conveying contaminant exposure levels derived by the exposure condition determination module 102 in order to derive degradation curves associated with different locations along the surface of the concrete structure. In a specific example of implementation, the derived degradation curves convey probabilities of initiation of corrosion of rebar (which may be caused for example by chloride ingress in the concrete structure under test) as a function of elapsed (future) time. In performing this processing, the probabilistic layer module 104 makes use of the concrete degradation modeling engine 106 in order to derive simulation data for estimating future degradation associated with different sets of specific simulation parameters. The probabilistic layer module 104 combines the individual simulations generated by the concrete degradation modeling engine 106 to derive information conveying a level of degradation risk by performing a reliability analysis based on the statistical moments of the individual simulations.

In a non-limiting example of implementation, the model used by the probabilistic layer module 104 and implemented by the concrete degradation modeling engine 106 may take into account one or more of the following properties of the concrete material: moisture transport characteristics, coupled diffusive fluxes, chemical reactions involving multiple species, temperature effect on transport and chemical reactions, and feedback effect between transport properties and chemical reactions. In a specific example of implementation, the model may be based upon a deterministic physico-chemical degradation model, such as the one implemented by the software application commercialized by SIMCO Technologies Inc. under the name of STADIUM® (shown in FIGS. 1 and 4 as module 106). Generally speaking, such a probabilistic layer (used by the probabilistic layer module 104) relies on point estimators to calculate the statistical moments of the response of the model, based upon given input variability. For example, the Rosenblueth point estimators method for probabilistic analysis may be used in specific practical implementations. For additional information pertaining to this method, the reader is invited to refer to E. Rosenblueth. "Two-point estimates in probabilities", *Applied Mathematical Modeling*, 5:329-335, 1981. The contents of the aforementioned document are incorporated herein by reference.

In a specific practical example of implementation, the probabilistic layer module 104, using the concrete degradation modeling engine 106, derives information conveying probabilities of initiation of corrosion of rebar in the concrete structure under test over time based on the location-dependent information received at input 114 and the contaminant exposure levels derived by exposure condition determination module 102. In a specific implementation, the determination of the risk (i.e. the likelihood that corrosion of rebar has been initiated) is solved as a reliability problem, where the solicitation is the chloride content, and the resistance is the chloride threshold necessary for corrosion initiation at the rebar level. In specific non-limiting practical implementations, such a reliability problem may be solved using a first-order reliability method (FORM), for example using a method such as an improved Hasofer & Lind, Rackwitz & Fiessler algorithm (iHLRF).

FIG. 8 shows a graph 500 depicting a sample degradation curve, which may be derived by the probabilistic layer module 104 and which conveys probabilities of initiation of corrosion of rebar caused by chloride ingress in the concrete structure under test as a function of elapse (future) time. The points on the curve shown in graph 500 are derived from relationships (depicted graphically in graphs 502a, 502b and 502c for three specific points on the curve 500) between a modeled chloride content level after a specific amount of time has elapsed and a threshold chloride content level.

In a specific example of implementation, the curve shown in graph 500 is derived by the probability layer module 104 which sends queries to the concrete degradation modeling engine 106 providing that engine with parameters based on the location-dependent information (based on information received at input 114) and information conveying contaminant exposure levels associated with the concrete structure under test (derived by exposure condition determination module 102). The concrete degradation modeling engine 106 is programmed for processing the received information in order to simulate an expected level of chloride ingress in the concrete structure under test for different time delays. In a specific example, multiple queries may be sent to the degradation modeling engine 106 to derive likelihoods of chloride content at specific locations of interest along the concrete structure under test and at different times in the future. In another specific example, multiple queries may be sent to the degradation modeling engine 106 to derive likelihoods of chloride content that account for all locations of the structure along the concrete structure under test and at different times in the future.

The practical representation of a degradation curve, as shown in FIG. 8 is the risk that a given specific location on the concrete structure under test is affected by the type of degradation mechanism being modeled.

In an exemplary implementation in which the location-dependent information received at input 114 conveys thickness measurement of the concrete cover over the reinforcing steel at different locations along the surface of the concrete structure under test, respective degradation curves may be derived by the probabilistic layer and associated with different locations along the surface of the concrete structure. In a non-limiting example, the surface of the concrete structure may be divided into sub-surfaces that have equal areas. In a practical case, each subsurface may represent an area of 100 to 900 $cm^2$ (approx. 16 to 144 $in^2$). In a non-limiting example, for each subsurface, a degradation curve may be derived in accordance with the process described above in part based on the rebar depth (which corresponds in this example to the thickness measurement of the concrete material over the reinforcing steel associated with the subsurface conveyed by the location-dependent information received at input 114).

Concrete Degradation Modeling Engine—Module 106

In a specific practical example of implementation, the concrete degradation modeling engine 106 used by the degradation simulation unit 18 implements a reactive transport model that uses mass conservation equations to describe degradation mechanisms considered in one specific analysis. Reactive transport models have been proposed in the past. For a specific example of a reactive transport model, the reader is invited to refer to U.S. Pat. No. 6,959,270, issued to J. Marchand et al. on Oct. 25, 2005 and entitled "*Method for modeling the transport of ions in hydrated cement systems*". The contents of the aforementioned document are incorporated herein by reference. In the context of the present invention, the modeling engine 106 uses parameters provided by the probabilistic layer module 104 to simulate a specific degradation mechanism on a given concrete material over a certain time delay. In a specific example, the parameters provided include materials properties, geometry of the simulated concrete element, and environmental conditions. When calculations are finished, the information derived and released by the modeling engine 106 is sent to the probabilistic layer module 104. In a specific example, the type of degradation mechanism considered by the concrete degradation modeling engine 106 is the corrosion of steel reinforcement bars embedded in concrete structure. In that case, the modeling engine 106 makes use mathematical models associated with the transport of chloride chemical inside concrete due to an external exposure (seawater, de-icer salts, etc.) in order to determine when steel corrosion is likely to be initiated. In a specific example, the output information generated by the modeling engine 106 conveys the derived results for a given time and a specific location in the concrete structure. The derived results can include (but are not restricted to) the concentration of chemical species in the pore solution, mineral phase contents, temperature, humidity, moisture saturation level in the concrete material, chloride content and the like. A non-limiting example of a commercially available concrete degradation modeling engine 106 that may be used is a service-life prediction software commercialized by SIMCO Technologies Inc. under the trademark STADIUM®.

Output Analysis/Degradation Calculation—Module 108

The output analysis/degradation calculation module 108 receives, from the probabilistic layer module 104, degradation curves associated with different locations along the surface of the concrete structure, of the type depicted in FIG. 8. The output analysis/degradation calculation module 108 processes these curves and derives information conveying degradation and durability characteristics of the concrete structure under test.

In a first specific example of implementation, the degradation and durability characteristics derived by module 108 convey a probability of corrosion initiation at different locations on the surface of the concrete structure under test. Such information can readily be derived by processing the specific degradation curves associated with different locations on the surface of the concrete structure. The probability of corrosion initiation at different locations on the surface of the concrete structure under test may be associated with the current time period or, alternatively may be associated with one or more future time period. The time period may vary and may be selected by default by the system 150 (wherein one or more time periods may be programmed in system 150) or based on information received by the system 150 through a user input (not shown) in order to provide the user with increased control and flexibility in viewing simulated degradation results over different time periods. Practical system will generally provide simulations for time periods that correspond to at least the projected service life of the structure (for example 10, 25, 50, 100 years). In addition, it is to be appreciated that while certain specific examples of time periods have been given for the purpose of example, any other suitable time period may be used. It is also to be appreciated that the probability of corrosion initiation at different locations on the surface of the concrete structure under test may be associated with multiple future time periods in order to convey an evolution over time period of the degradation and durability characteristics.

FIG. 9 of the drawings shows in graphical form information conveying a current (time delay=0 years) probability of corrosion initiation at different locations on the surface of the concrete structure under test. It is to be appreciated that when the structure under test is an existing structure, it would have been exposed in the past (for a known duration) to contaminant levels. As such, the current probability of corrosion initiation is a result of this past exposure. As shown, dark areas correspond to locations on the surface of the concrete structure under test where corrosion is most likely to have been initiated while lighter areas correspond to areas associated with a lesser probability of corrosion being initiated.

FIG. 10 of the drawings shows in graphical form information conveying a probability of corrosion initiation at different locations on the surface of the concrete structure under test after a time period of 50 years has elapsed. As shown, dark areas correspond to locations on the surface of the concrete structure under test where corrosion is most likely to have been initiated while lighter areas correspond to areas associated with a lesser probability of corrosion being initiated.

In a non-limiting example, the time duration shown in box 950 shown in FIGS. 9 and 10 can be specified by a user of the system, for example by providing a user operable control to allow the user to specify a time period for which degradation simulation is desired. In such implementation, the time duration may be specified by a user by using, for example, a touch sensitive screen, keyboard, mouse, voice input, user created data file or the like to provide information conveying the time period for which the degradation simulation associated with the concrete structure under test is desired. In a non-limiting implementation, box 950 is a user editable text field allowing the user to specific a time delay.

In a second specific example of implementation, the degradation and durability characteristics derived by module 108 convey a proportion (or fraction) of the surface of the concrete structure under test likely to be affected by a given level of degradation corrosion as a function of time. In a specific example of implementation such information may be derived by processing the degradation curves associated with different locations on the surface of the concrete structure to calculate, over time, the portion of the surface that is at or above a given risk of degradation. In this specific example, the degradation level of each subsurface is analyzed and the number of subsurfaces that are above the degradation threshold for the chosen degradation level e.g. medium or heavy—is used to derive the portion of the overall surface affected by that degradation level.

FIG. 11 is a graphical representation of estimated degradation and durability characteristics of a concrete structure under test that may be displayed in accordance with the above described second specific example of implementation.

More specifically, the graph 1050 shown in FIG. 11 conveys what portion (or fraction) of the concrete structure would likely be affected at a given degradation level after different time delays over time. In this example, two degradation levels are shown (medium degradation level 1000 and heavy degradation level 1010). In addition, a total degradation 1020, which essentially amounts to the sum of the medium degradation level 1000 and heavy degradation level 1010, is also shown on the graph 1050. In this specific example, the graph 1050 conveys that after about 42 years, about 20% of the surface of the concrete structure under test is likely to show signs of medium or heavy degradation. The degradation levels displayed on graph 1050 may be pre-programmed in system 150, and (or) may be specified by a user of the system 150 through are user operable control, such as for example touch sensitive screen, keyboard, mouse, voice input, user created data file or the like. While this specific example shows two degradation levels in graph 1050, any number of user selectable degradation levels can be tracked over time depending on the specific implementation. Advantageously, allowing a user to specify what degradation levels are to be displayed, provides the user with increased control and flexibility in viewing simulated degradation results over different time periods.

The output analysis/degradation calculation module 108 releases information conveying the derived degradation and durability characteristics of the concrete structure under test at output 34.

Example of a Process that May be Implemented by the Concrete Degradation Simulation Unit 18

An example of a process that may be implemented by the concrete degradation simulation unit 18 of the type shown in FIG. 6 will now be described with reference to FIGS. 6, 12A, 12B, 12C and 12D to illustrate the interactions between components and how degradation and durability characteristics of the concrete structure under test may be derived by the concrete degradation simulation unit 18.

Figure 12A:
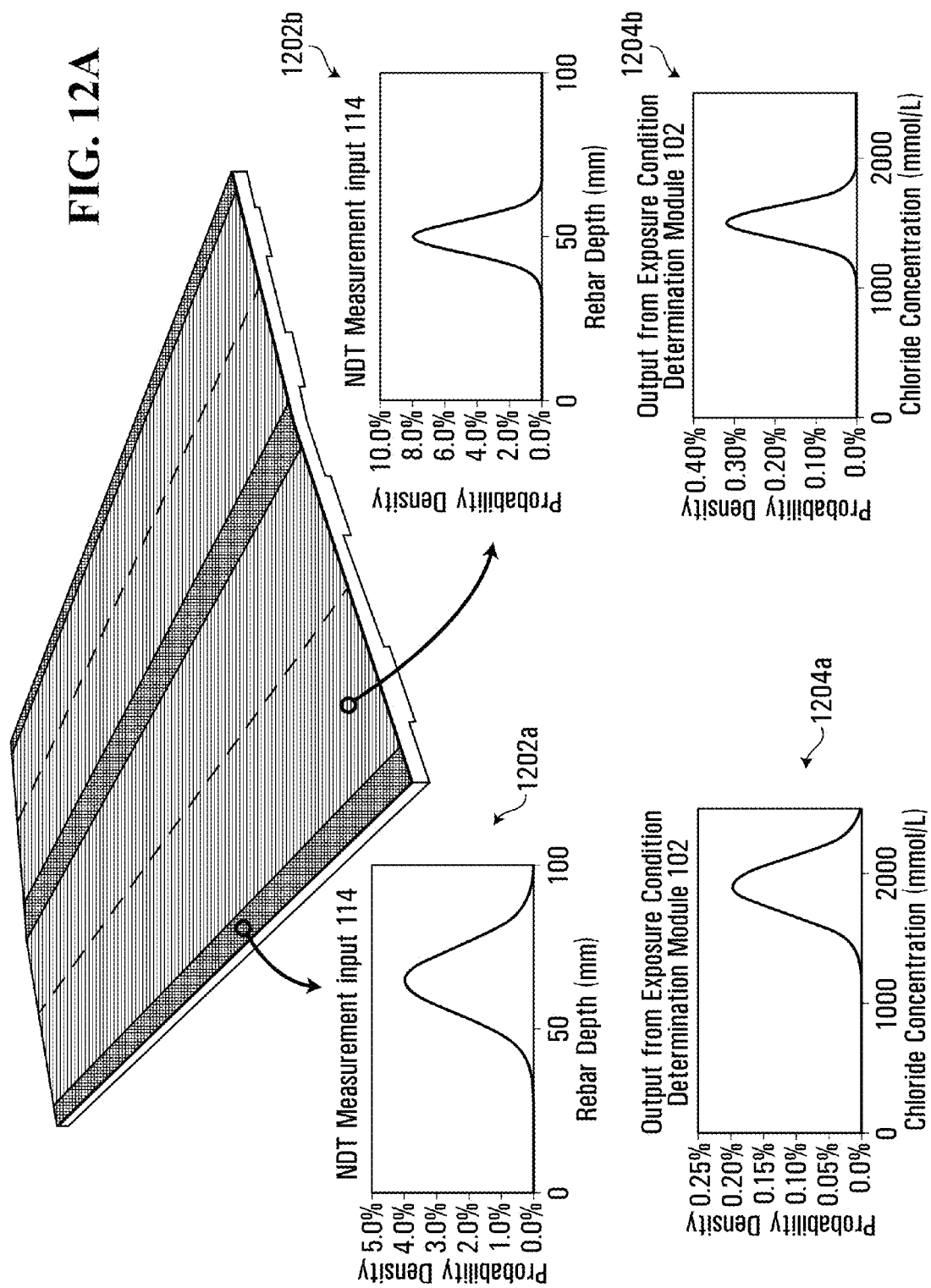
FIGS. 12A, 12B, 12C and 12D are graphical representations of a process implemented by the components of the concrete degradation simulation unit of the type depicted in FIG. 6 in accordance with a non-limiting example of implementation of the invention.

In a specific, non-limiting example, the process implementation by the concrete degradation simulation unit can be described as follows:

First, information is received from the set of inputs 44 providing structural, material and environmental information associated with the structure under test. In a specific example, the information includes location-dependent information conveying structural information (received at input 114) obtained by applying a non-destructive testing (NDT) process to the concrete structure under test, information conveying material properties (received at input 10) and information conveying estimated environmental conditions to which the concrete structure under test is subjected (received at input 12). In a specific implementation, the information received at the set of inputs 44 includes indications of uncertainty of the measurements, if applicable. This information is processed by the exposure condition determination module 102 to derive exposure parameters conveying contaminant exposure levels at different locations along the surface of the concrete structure. The information received at the set of inputs 44 and derived by the exposure condition determination module 102 is associated with different subsurfaces (or areas) of the virtual model 46 of the concrete structure under test. FIG. 12A graphically illustrates such information with respect to a specific concrete structure. In this specific example, the material properties are taken as being uniform for the whole virtual model of the concrete structure, but there are two different exposure condition zones associated with respective exposure parameters 1204a and 1204b conveying contaminant exposure levels (in this example the zones along the longitudinal sides of the structure and along the centerline zone have higher external chloride exposure). In addition, in this example, location-dependent information (received at input 114), designated by reference numerals 1202a and 1202b, is associated with the two different zones of the concrete structure.

Figure 12B:
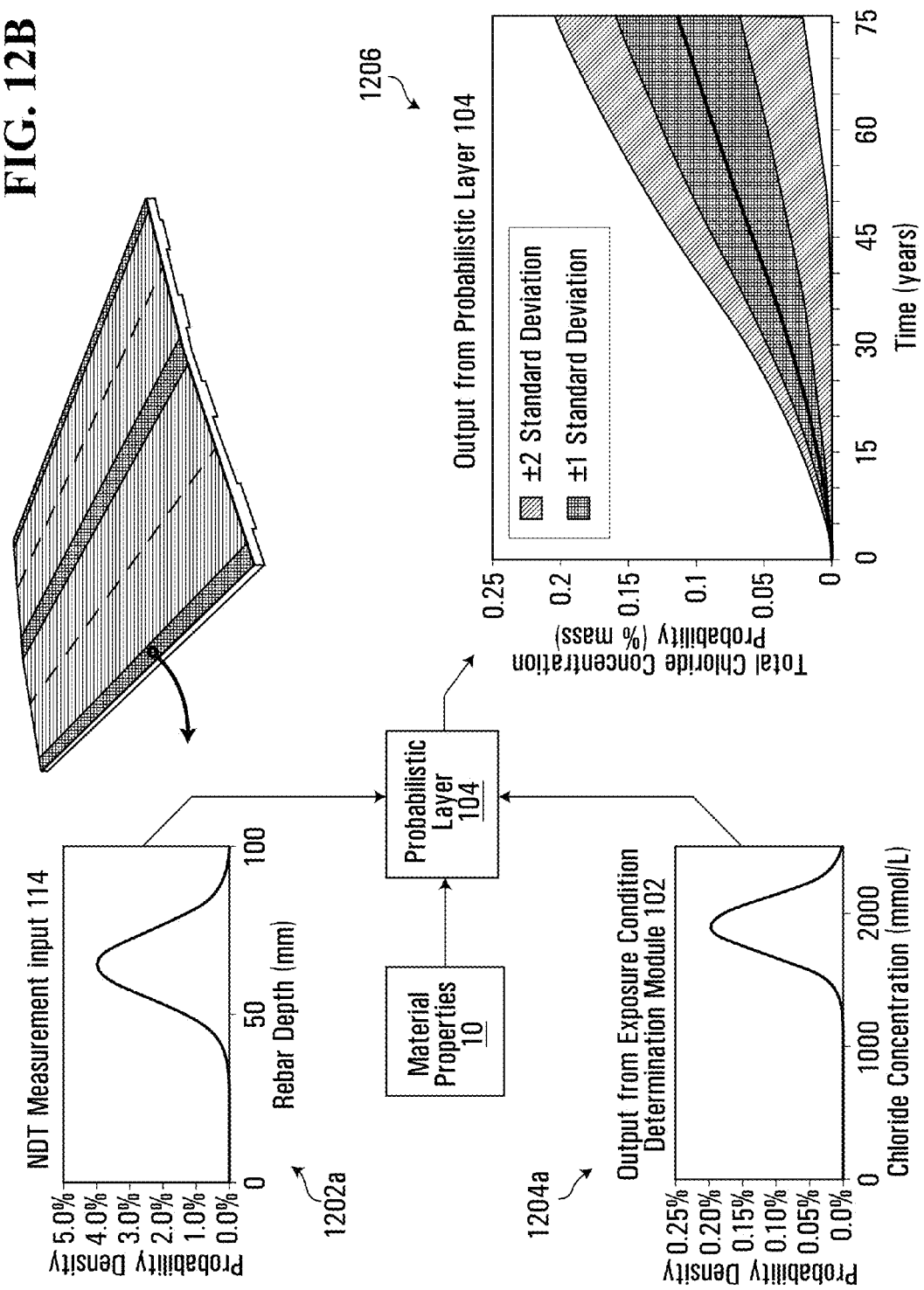

Following this, the probabilistic layer 104 (shown in FIG. 6) processes the information received at the set of inputs 44 and the exposure parameters conveying contaminant exposure levels derived by the exposure condition determination module 102 to derive degradation curves associated with different locations along the surface of the concrete structure. FIG. 12B graphically illustrates information processed and derived by the probabilistic layer 104 for a zone of the specific concrete structure under test. More specifically, to derive the probabilistic output 1206 associated with a zone along one of the longitudinal side of the structure (as shown in FIG. 12B), the probabilistic layer 104 processes the location-dependent information conveying structural information 1202a (received at input 114), the material properties (received at input 10), environmental condition information (received at input 12—not shown in FIG. 12B) and the information conveying contaminant exposure levels 1204a (derived by the exposure condition determination module 102). The modeling illustrated in FIG. 12B derives the total chloride concentration probability for each zone (or subsurface). It is noted that similar processing is performed for the different zones of the concrete structure under test using the appropriate location depending information and contaminant exposure levels for each of the respective zones. The probabilistic layer 104 may also uses the location-dependent information (received at input 114, in this specific example, GPR data of the rebar depth) to derive the total chloride concentration probability at the correct depth for the calculation of the corrosion risk of the rebar. This probabilistic modeling may be performed using Rosenblueth Point Estimators, as suggested earlier in the present document.

Figure 12C:
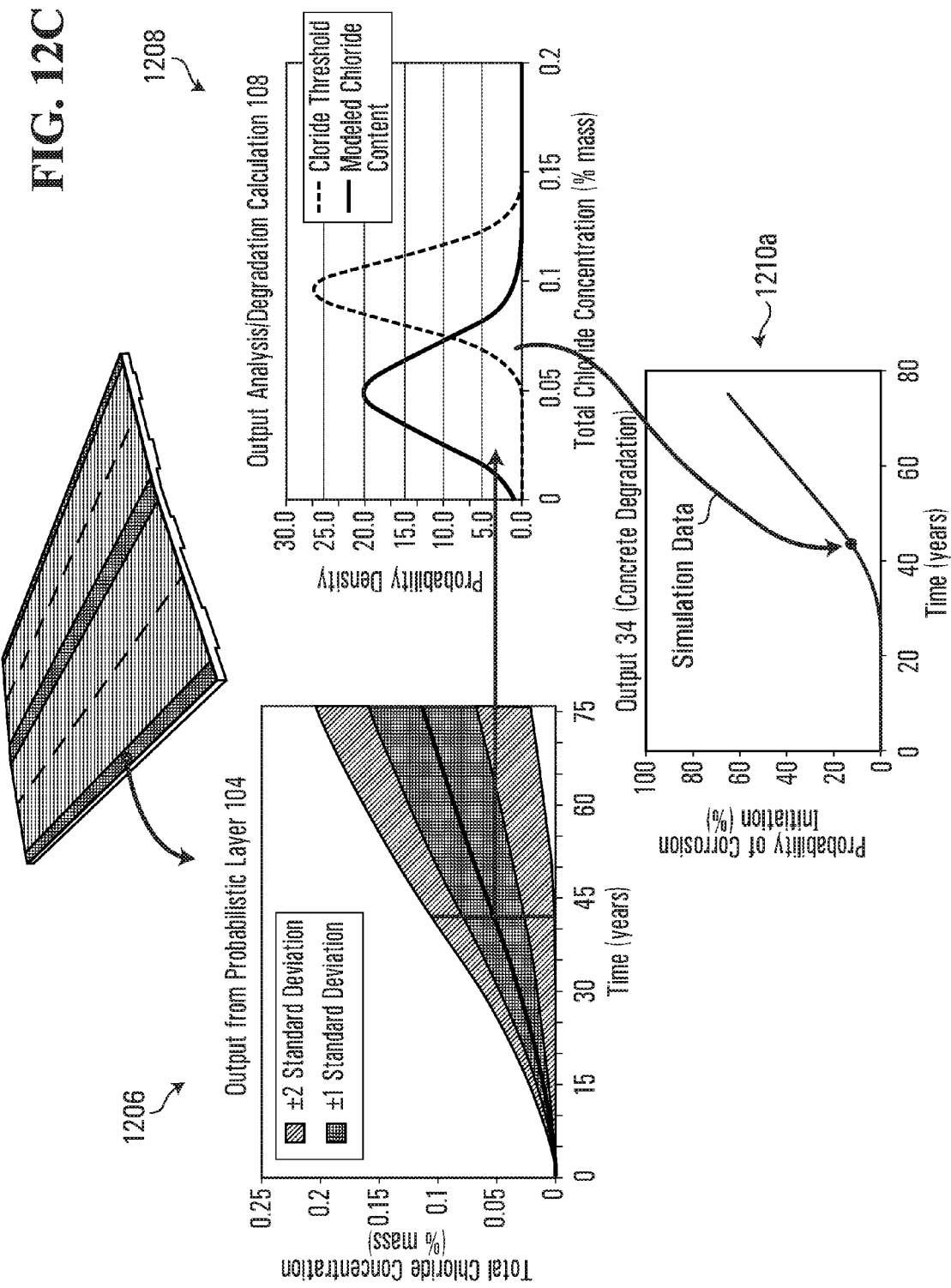

The probabilistic contaminant content associated with different locations along the surface of the concrete structure are then processed by the probabilistic layer 104 to derive information conveying degradation and durability characteristics of the different zones of the concrete structure. In this specific example, the simulated (modeled) probabilistic chloride content as a function of time (as conveyed by graph 1206) is processed by the probabilistic layer 104 for each zone and compared to a threshold chloride content, in this case a chloride threshold for the initiation of corrosion in steel rebar. This may be solved by considering this to be a reliability problem and solving it using first-order reliability method (FORM) and an improved Hasofer & Lind, Rackwitz & Fiessler algorithm (iHLRF). For a formal description of the iHLRF method, the reader is invited to consult the chapter by Der Kiureghian, A. (2005) entitled "First- and second-order reliability methods." in *Engineering Design Reliability Handbook*, E. Nikolaidis, D. M. Ghiocel, and S. Singhal, eds., CRC Press. The contents of the aforementioned document are incorporated herein by reference. FIG. 12C graphically illustrates information processed and derived by the probabilistic layer 104 for one specific zone of the concrete structure. Graph 1208 in FIG. 12C shows a qualitative representation of the failure domain between the chloride content and chloride threshold probability curves, and the resulting point on the corrosion initiation risk curve for a specific subsurface. It is to be noted that the area of intersection between the two curves does not directly convey a likelihood of initiation of corrosion of the steel rebar. Rather, in order to obtain an indication of such likelihood, a calculation such as the FORM calculation mentioned above may be used for the service life of the structure and for the individual subsurfaces.

Figure 12D:
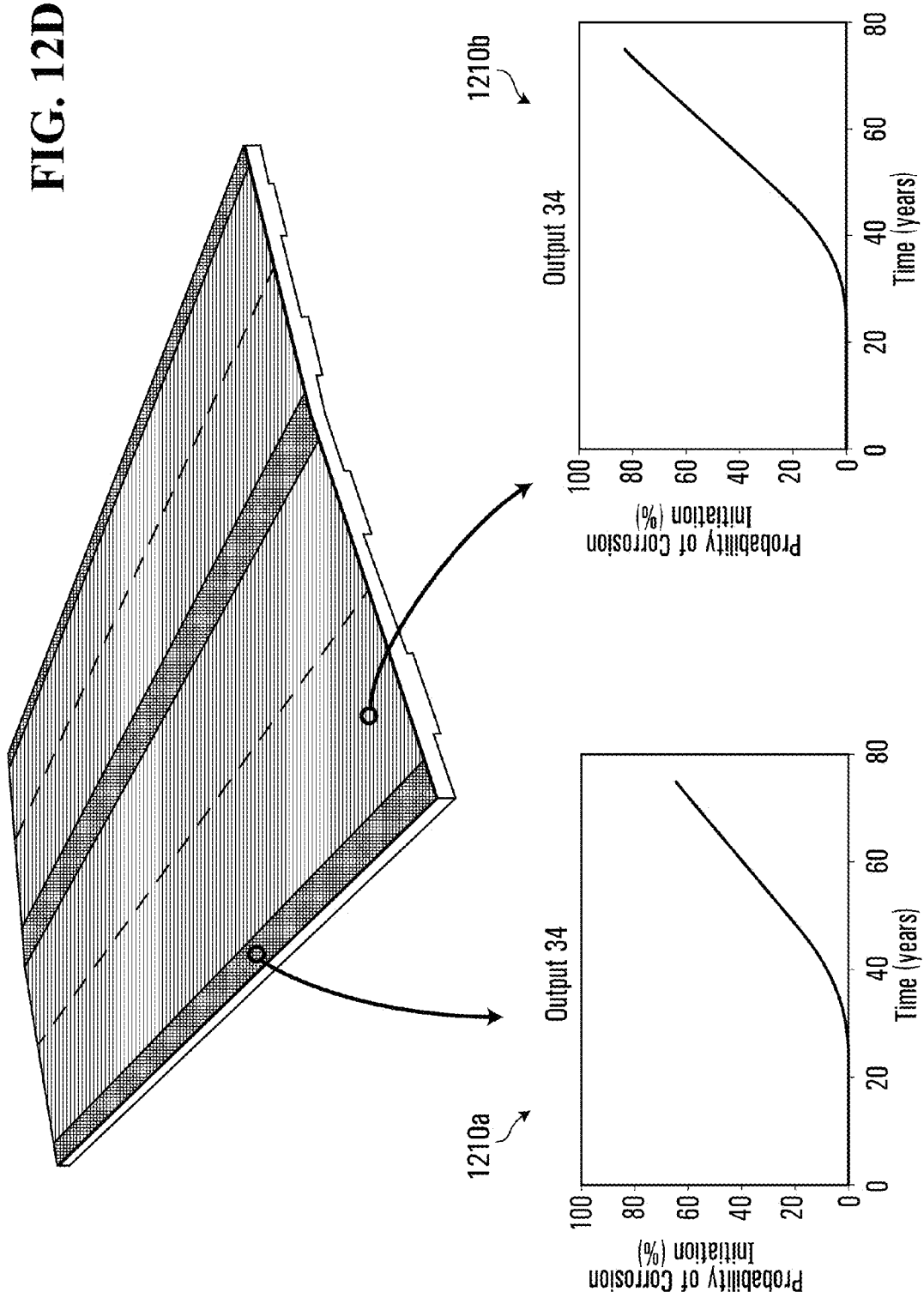

The information conveying degradation and durability characteristics 1210a derived by the probabilistic layer 104 are then provided to the output analysis/degradation calculation module 108. It is to be appreciated that the process described above summarizes a specific example for the modeling of a specific type of degradation mechanism, namely chloride ingress. This process may be repeated for other types of degradation mechanisms, for which the degradation results may be concurrent or cumulative. Additional degradation mechanisms may be considered by the output analysis degradation calculation module 108. This module 108 assigns the individual degradation curves to specific locations of the virtual model of the structure under test 46. Each different subsurface of the concrete structure under test is assigned a specific degradation curve for a specific type of degradation mechanism. FIG. 12D shows information conveying degradation and durability characteristics 1210a and 1210b assigned by the output analysis/degradation calculation module 108 for two different subsurfaces of the virtual model of the concrete structure under test.

Variant—Repair Scenario Modeling and Asset Management Strategy

Optionally, the system 150 depicted in FIG. 1 may be augmented to provide other features in connection with estimating and predicting degradation and durability characteristics of concrete structures under test.

Figure 13:
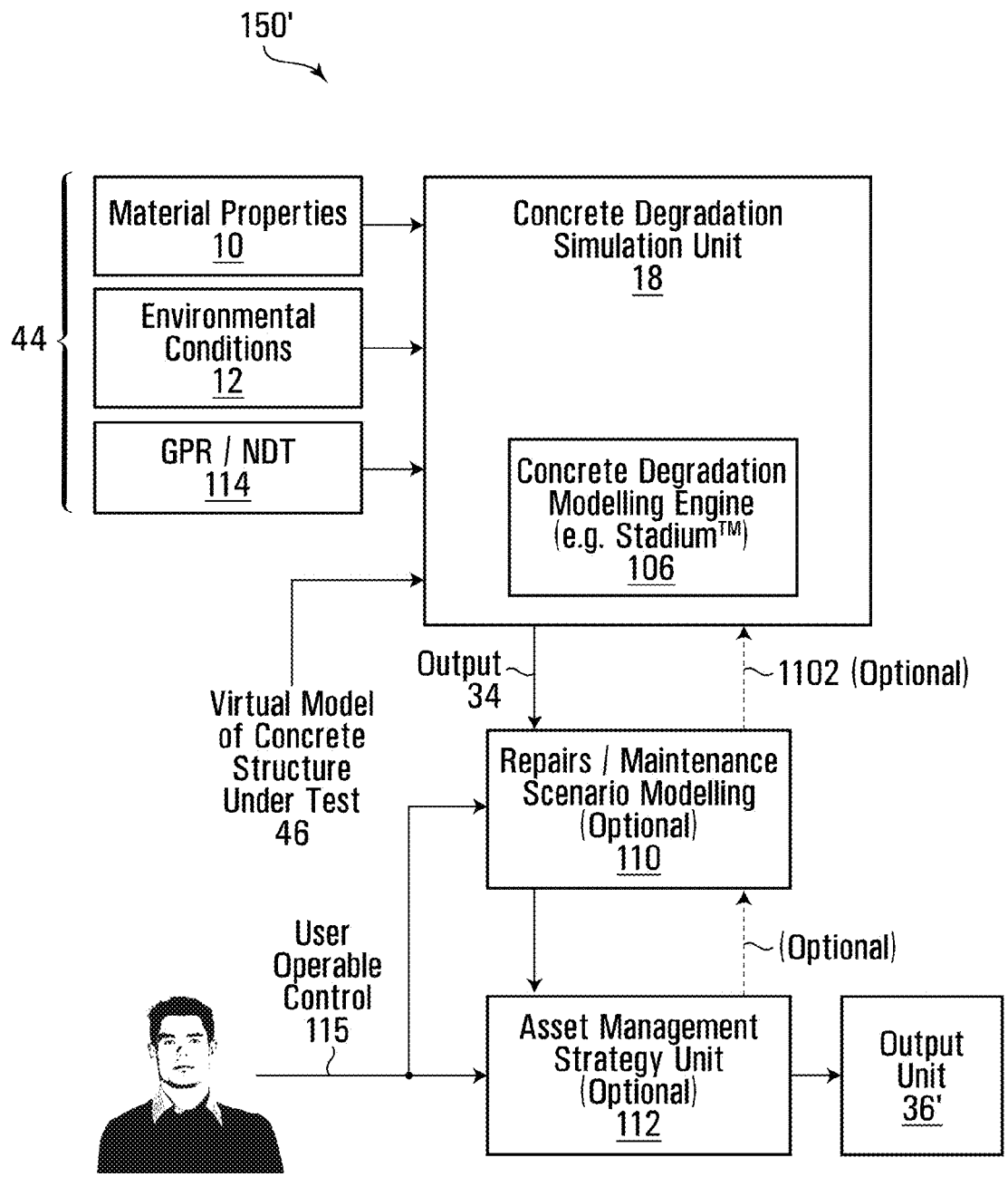
FIG. 13 shows a block diagram of a system for estimating degradation and durability characteristics of a concrete structure under test in accordance with an implementation of a specific variant of the invention.

A variant of the system 150 depicted in FIG. 1 is depicted in FIG. 13 of the drawings and is designated as system 150'. As depicted in FIG. 13, the system 150' includes components similar to those of system 150 shown in FIG. 1 namely: a set of inputs 44 for receiving information associated with a specific concrete structure under test, a concrete degradation simulation unit 18 for processing the information received at the set of inputs 44 to derive concrete degradation simulation data conveying estimated degradation and durability characteristics associated with the concrete structure under test. In this variant, the system 150' also includes a repairs/maintenance scenario modeling unit 110 for estimating degradation and durability characteristics associated with the concrete structure under test under different repair and maintenance scenarios. In this variant, the system 150' may also optionally include an asset management strategy unit 112 for assisting a manager of a concrete structure to plan maintenance activities over time. The system 150' also includes an output unit 36', analogous to output unit 36 shown in FIG. 1.

Repair/Maintenance Scenario Modeling Unit 110

In the specific variant depicted in FIG. 13, the repair/maintenance scenario modeling unit 110 is configured to simulate degradation by taking into account potential maintenance/repair scenario susceptible to be performed on the concrete structure under test.

In a specific implementation, the repair/maintenance scenario modeling unit 110 is configured for processing data received at inputs 10 and 114, specifically the modified material properties (based on the information received at input 10) and modified location-dependent information (based on the information received at input 114) to account for different materials and structure that may be associated with maintenance/repairs of the structure. The modified properties and modified location-dependent information may be pre-defined scenarios implemented by the repair/maintenance scenario modeling unit 110 and/or they may be specified by a user of the system 150' through one or more user operable control 115. The person skilled in the art will readily appreciate that in implementation in which a user may enter desired potential modifications, a suitably configured graphical user interface may be displayed on a display device for facilitating entry of information conveying such desired maintenance/repairs scenario using a user operable input control 115, such as for example touch sensitive screen, keyboard, mouse, voice input, user created data file or the like.

The modified material properties and the modified location-dependent information are sent to the concrete degradation simulation unit 18 (as illustrated by arrow 1102) which in turn repeats the process of deriving degradation and durability characteristics of the concrete structure under test (in the manner described above) using the modified parameters. As a result, the degradation and durability characteristics of the concrete structure under test derived in this manner and released at output 34 may therefore take into account potential maintenance/repair scenarios. This process can be repeated for multiple repair scenarios by repeatedly providing the concrete degradation simulation unit 18 with different versions of the modified material properties and modified location-dependent information. In such a variant, the concrete degradation simulation unit 18 would be configured to have capabilities for handling two or more concrete layers, each layer being characterized by a respective thickness and set of material properties.

Figure 14A:
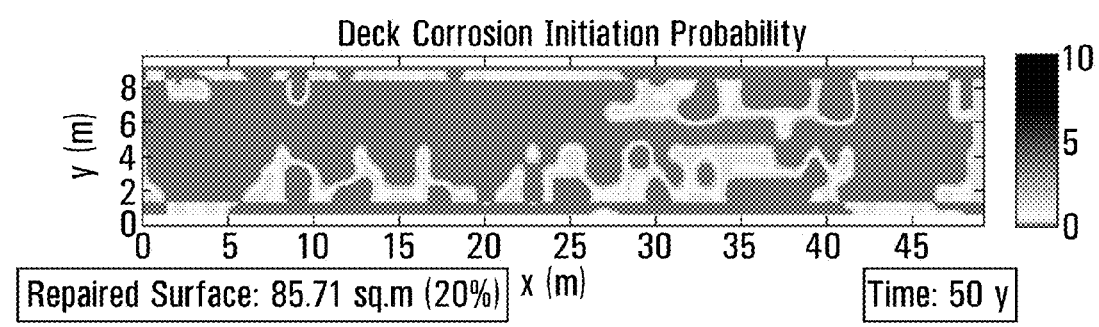
FIGS. 14A and 14B are graphical representations of estimated degradation and durability characteristics of a concrete structure under test for two different repair scenarios after a time delay of 50 years has elapsed in accordance with a specific example of implementation of the invention. In this example, the estimated degradation and durability characteristics convey a probability of corrosion initiation at different locations on the surface.
Figure 14B:
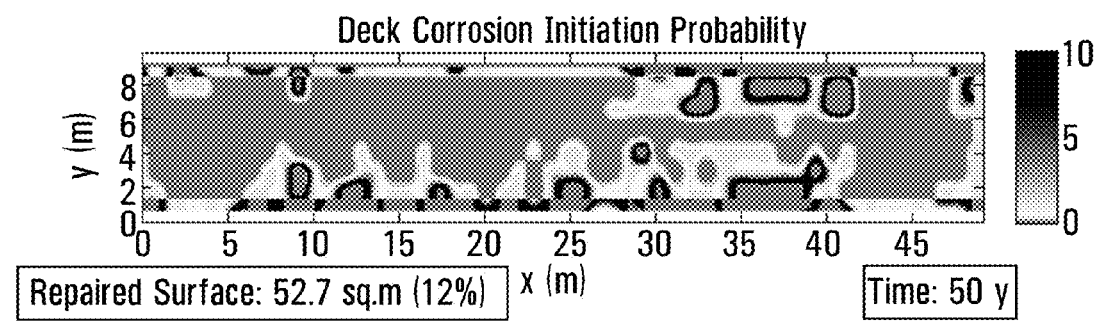

FIGS. 14A and 14B are graphical representations of estimated degradation and durability characteristics of a concrete structure under test for two different repair scenarios after a time delay of 50 years has elapsed in accordance with a specific example of implementation of the invention. In this example, the estimated degradation and durability characteristics convey a probability of corrosion initiation at different locations on the surface.

Figure 15A:
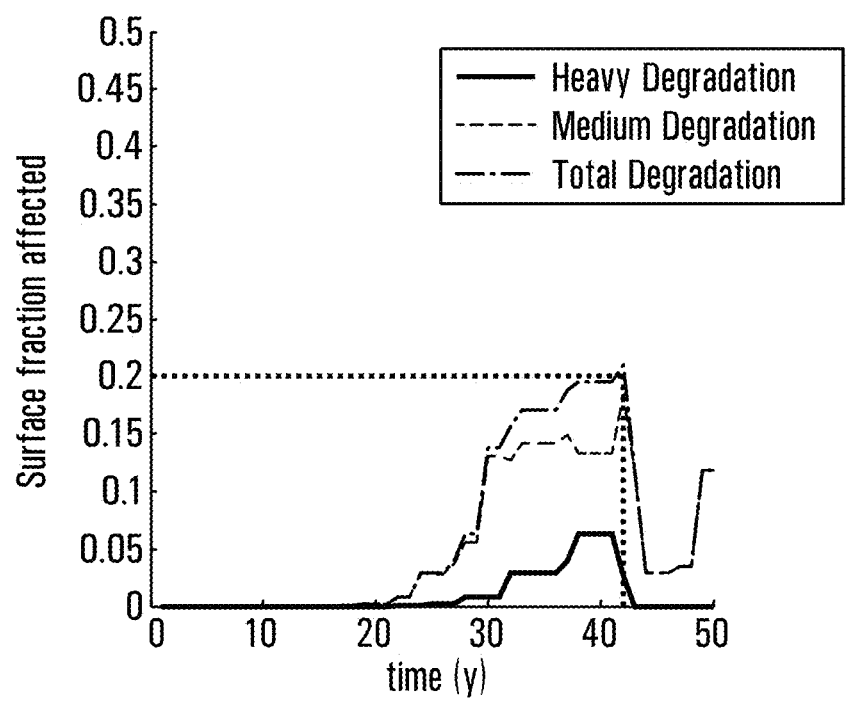
FIGS. 15A and 15B are graphical representations of estimated degradation and durability characteristics of a concrete structure under test for two different repair scenarios in accordance with another specific example of implementation of the invention. In this example, the estimated degradation and durability characteristics convey what fraction of the structure would likely be affected by a given degradation level after different time delays and assuming different levels of degradation for each of the repair scenarios.
Figure 15B:
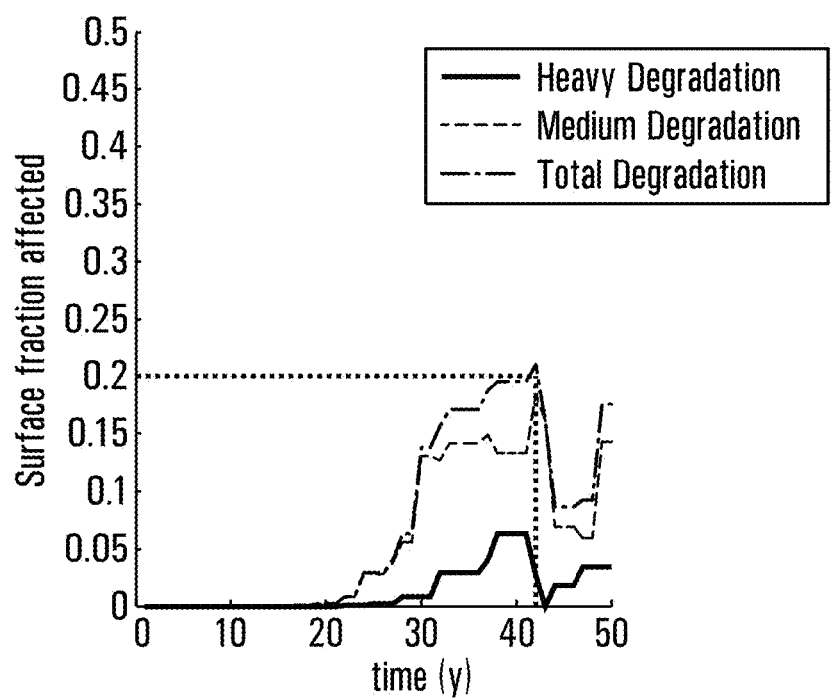

FIGS. 15A and 15B are graphical representations of estimated degradation and durability characteristics of a concrete structure under test for two different repair scenarios in accordance with another specific example of implementation of the invention. In this example, the estimated degradation and durability characteristics convey what portion (or fraction) of the structure would likely be affected by a given degradation level after different time delays and assuming different levels of degradation for the same repair scenarios depicted with reference to FIGS. 14A and 14B.

Asset Management Strategy Unit 112

In a specific variant of the system 150, the repair/maintenance scenario modeling unit 110 releases the derived simulated degradation and durability characteristics of the concrete structure under test to the asset management strategy unit 112. In a specific implementation, the asset management strategy unit is configured to process the derived simulated degradation and durability characteristics under the different maintenance/repairs scenario in combination with various criteria in order to assist a user in selecting a suitable maintenance approach for the concrete structure under test. The criteria considered by the asset management strategy unit 112 may vary from one implementation to the other and may include, without being limited to: costs associated with each repair scenario for maintaining the concrete structure over its useful life; minimal safety criteria; maximum allowable degradation threshold and the like.

In a specific example, the repair/maintenance scenario modeling unit 110 releases information at output 34 conveying estimated degradation and durability characteristics associated with two or more distinct repair scenarios, each repair scenario being associated with certain repairs being performed at specific time delays on a concrete structure. In this example, the asset management strategy unit 112 may be programmed to derive estimated costs associated with maintaining the concrete structure over its useful life under each of the two or more repair scenarios. In a specific example, this may be achieved by:

Calculating the maintenance cost, including but not limited to materials, workmanship, and necessary equipment for performing maintenance associated with a specific repair scenario;

Calculating the user cost associated with disturbance and stoppage of the concrete structure; and Correcting, with the discount rate, the net present value of future cash flows (NPV), based upon a reference interest rate.

Any suitable life-cycle cost calculation approach may be used to calculate the estimated costs associated with maintaining the concrete structure under each of the two or more repair scenarios. Manners in which life-cycle cost calculation associated with maintenance scenarios are well known by persons skilled in the art and are beyond the scope of this application and thus will not be described in further detail here.

The asset management strategy unit 112 may be further programmed to process the information conveying estimated degradation and durability characteristics released at output 34 under each one of the two or more maintenance/repair scenarios to assess whether levels of degradation conveyed by such information comply with maximum allowable levels of degradation during the useful life of the concrete structure. The maximum allowable levels of degradation can be considered as conveying an acceptable level of risk and may be defined by the user of the system, by pre-determined guidelines and/or by default values programmed into the asset management strategy unit 112. For example, a maximum allowable level of degradation may be defined as a threshold portion fraction of the surface of the concrete structure being affected by either a medium or high level of degradation.

Given the maximum allowable levels of degradation, the two or more maintenance/repair scenarios can be processed by the asset management strategy unit 112 to identify one or more scenarios that achieve a desired objective, for example minimize costs associated to the maintenance of the concrete structure and falling under the maximum allowable levels of degradation. The specific manners in which selection of maintenance/repair scenarios may be performed may vary from one implementation to the other and will become apparent to persons skilled in the art. Such specific approaches are beyond the scope of the present application and therefore will not be described in further detail here.

Specific Practical Implementation

Figure 16:
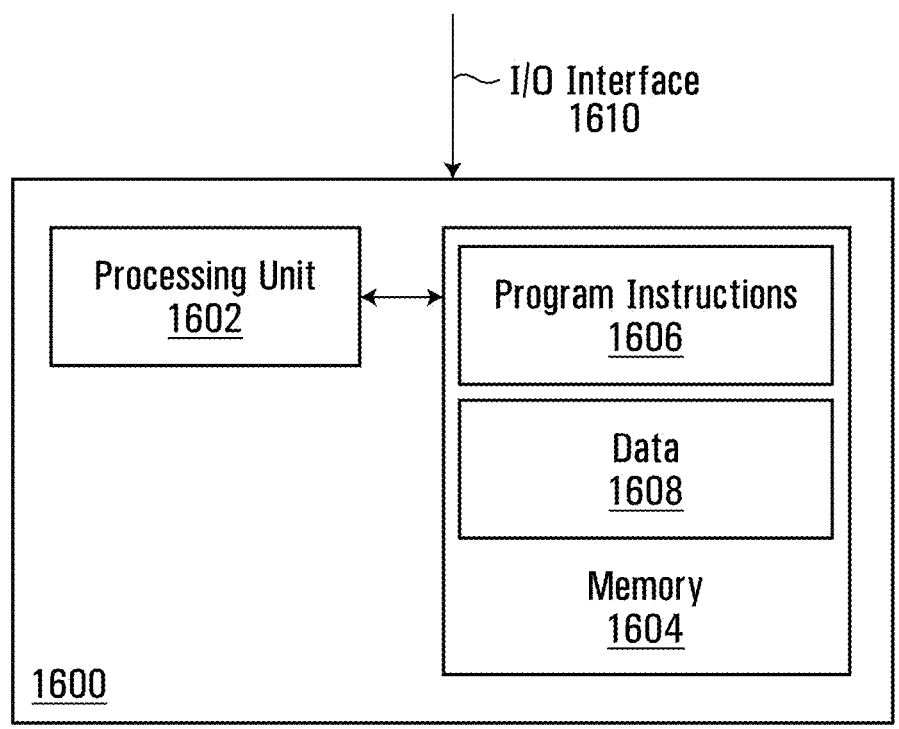
FIG. 16 is a simplified block diagram a computing device programmed for implementing at least a portion of the functionality of the system for estimating degradation and durability characteristics of a concrete structure under test shown in either one of FIG. 1 or 13 in accordance with a specific non-limiting example of implementation of the invention.

Certain portions of the system depicted in FIG. 1, and of the variant depicted in FIG. 13, may be implemented on a general purpose digital computer. FIG. 16 shows a simplified representation of a general purpose digital computer 1600 which includes a processing unit 1602 and a memory 1604 connected by a communication bus.

The memory 1604 stores data 1608 and program instructions 1606. The processing unit 1602 is configured to process the data 1608 and the program instructions 1606 in order to implement the functions described above and depicted in the drawings. For example, the data portion 1608 of the memory 1604 may store information conveying material properties associated with the concrete structures, data conveying environmental conditions and/or data derived using a non-destructive testing (NDT) process, such as a process using ground penetrating radar (GPR). The digital computer 1600 may also comprise an I/O interface 1610 for receiving and/or sending data elements to external devices. For example, some of the aforementioned information [e.g. material properties associated with the concrete structures, data conveying environmental conditions and/or data derived using non-destructive testing equipment (NDT), such as ground penetrating radar (GPR)] may be received from devices external to device 1600. In another example, I/O interface 1610 may be used to release a signal for causing estimated degradation and durability characteristics of the concrete structure under test, derived by using the processing unit 102 to execute the program instructions 1606, to be displayed on a display device (not shown in FIG. 16) in communication with the general purpose digital computer 1600.

Figure 17:
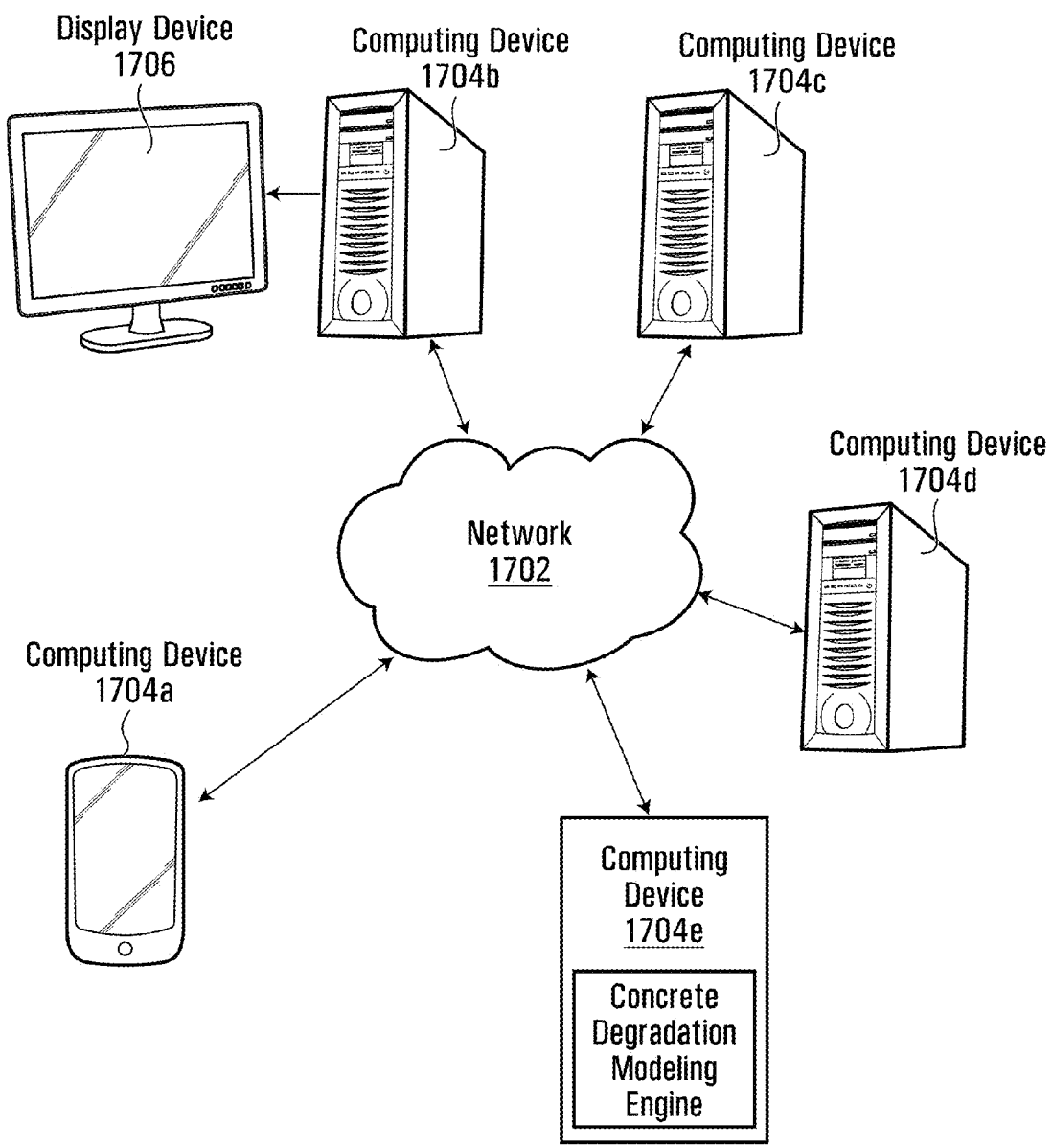
FIG. 17 is a simplified block diagram of a distributed computer network including a plurality of computing devices functionally interconnected over a computer network, the computing devices being programmed for implementing at least a portion of the functionality of the system for estimating degradation and durability characteristics of a concrete structure under test shown in either one of FIG. 1 or 13 in accordance with another specific non-limiting example of implementation of the invention.

It is to be appreciated that, in alternative an implementation of the type shown in FIG. 17, the system depicted in FIG. 1, as well as variants thereof including the variant depicted in FIG. 13, may be implemented by one or more computing devices 1704*a-e*, each including one or more processors, wherein the one or more computing devices 1704*a-e* are in communication with one another over a distributed computing network 1702. In such a network, data may be collected at one or more locations and transmitted over the network 1702 to one or more of the other computing devices, wherein the one or more of the other computing devices implement the functionality described with reference to the concrete degradation simulation unit 18 (shown in FIGS. 1 and 5). It will be appreciated that the functionality implemented by each of the components of the concrete degradation simulation unit 18, namely the exposure condition determination module 102, the probabilistic layer, the concrete degradation modeling engine 106 and the output analysis/degradation calculation module 108, may be implemented by a same computing device or by multiple computing devices functionally interconnected to one another. In the example depicted, the functionality of the concrete degradation modeling engine 106 is shown as being implemented by computing device 1704*e*. In addition, the results obtained by the one of more computing devices implementing the functionality described with reference to the concrete degradation simulation unit 18 and conveying estimated degradation and durability characteristics of the concrete structure under test may be transmitted to yet another computing device (or to the same computing device from which the data originated). The computing device to which the results are sent may then release a signal for causing the estimated degradation and durability characteristics to be displayed on a display device, such as display device 1706, so that information derived there from may be conveyed to a user.

The foregoing is considered as illustrative only of the principles of the invention. Since numerous modifications and changes will become readily apparent to those skilled in the art in light of the present description, it is not desired to limit the invention to the exact examples and embodiments shown and described, and accordingly, suitable modifications and equivalents may be resorted to. It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this invention pertains. In the case of conflict, the present document, including definitions will control.

The above description of the embodiments should not be interpreted in a limiting manner since other variations, modifications and refinements are possible and will become readily apparent to the person skilled in the art in light of the present description. The scope of the invention is defined in the appended claims and their equivalents.

APPENDIX I

For some examples of methods and devices useful for generating location-dependent information of the type mentioned above, the reader is invited to refer to the following documents:

- U.S. Patent Publication US2010/0052971A1 ("Amarillas"), published on Mar. 4, 2010 and directed to "Device and Method for Evaluate Condition of Concrete Roadways Employing a Radar-based Sensing and Data Acquisition System".
- U.S. Pat. No. 6,246,354 ("Liedtke et al."), issued on Jun. 12, 2001 and directed to "Method for Determining of Permittivity of Concrete and Use of the Method".
- U.S. Pat. No. 6,186,006 ("Schmitz et al."), issued on Feb. 13, 2001 and directed to "Method for three-Dimensional and Non-Destructive Detection of Structures".
- U.S. Pat. No. 6,429,802 ("Roberts"), issued on Aug. 6, 2002 and directed to "Determining the condition of a Concrete Structure using Electromagnetic Signals".
- U.S. Pat. No. 6,246,354 ("Liedtke et al."), issued on Jun. 12, 2001 and directed to "Method for Determining of Permittivity of Concrete and Use of the Method".
- U.S. Pat. No. 7,190,302 ("Biggs"), issued on Mar. 13, 2007 and directed to "Sub-surface Radar Imaging".
- U.S. Pat. No. 7,374,006 ("Boehm"), issued on May 20, 2008 and directed to "Method and Device for Determining the Roadway Condition".
- U.S. Pat. No. 7,937,229 ("Buyukorturk et al."), issued on May 3, 2011 and directed to "System and Method for Detecting Damage, Defect, and Reinforcement in Fiber Reinforced polymer Bonded Concrete Systems Using Far-Field Radar".

The contents of the aforementioned documents are incorporated herein by reference.

The invention claimed is:

1. A method for estimating degradation and durability characteristics of a concrete structure under test, the concrete structure under test being a reinforced concrete structure, the method being implemented by a system including at least one programmable processor and comprising:
   a) receiving location-dependent information associated with the concrete structure under test and conveying structural information associated with different locations along the concrete structure under test, the location-dependent information having been obtained by applying a non-destructive testing (NDT) process to the concrete structure under test;
   b) processing the location-dependent information associated with the concrete structure under test in combination with:
      i) information conveying material properties associated with the concrete structure under test; and
      ii) information conveying estimated environmental conditions to which the concrete structure under test is subjected;
   the processing being for deriving concrete degradation simulation data, the derived concrete degradation simulation data information conveying estimated degradation and durability characteristics associated with at least some of the different locations along the concrete structure under test;
   c) releasing a signal for causing the estimated degradation and durability characteristics of the concrete structure under test to be displayed on a display device in communication with the system.

2. A method as defined in claim 1, wherein the concrete degradation simulation data conveys current estimated degradation and durability characteristics associated with the different locations along the concrete structure under test.

3. A method as defined in claim 1, wherein the concrete degradation simulation data conveys an evolution over a time period of the estimated degradation and durability characteristics associated with the different locations along the concrete structure under test.

4. A method as defined in claim 3, wherein the time period is at least 10 years.

5. A method as defined in claim 4, wherein the time period is at least 25 years.

6. A method as defined in claim 5, wherein the time period is at least 50 years.

7. A method as defined in claim 3, wherein the time period is specified by a user of the system.

8. A method as defined in claim 7, said method comprising receiving from a user interface device information conveying the time period.

9. A method as defined in claim 1, wherein at least a portion of the information conveying material properties associated with the concrete structure is derived based on analysis applied to a set of cores extracted from the concrete structure under test.

10. A method as defined in claim 1, wherein the information conveying estimated environmental conditions to which the concrete structure under test is subjected conveys temperature information.

11. A method as defined in claim 1, wherein the information conveying estimated environmental conditions to which the concrete structure under test is subjected conveys information related to humidity levels.

12. A method as defined in claim 1, wherein the information conveying estimated environmental conditions to which the concrete structure under test is subjected conveys information related to exposure to aggressive agents.

13. A method as defined in claim 1, wherein the structural information conveyed by the location-dependent information convey a state of the materials out of which the concrete structure under test is built.

14. A method as defined in claim 13, wherein the structural information associated with different locations along the concrete structure under test and conveyed by the location-dependent information includes at least one of:
- location and surface area of delaminated material;
- location and quantity of reinforcing steel;
- location of current corrosion activity;
- location of voids; and
- location and depth of existing repaired portions of the concrete structure under test.

15. A method as defined in claim 1, wherein the NDT process applied to derive the location-dependent information associated with the concrete structure under test includes using ground penetrating radar on the different locations along the concrete structure under test to derive the location-dependent information.

16. A method as defined in claim 1, wherein the concrete structure under test is comprised in part of concrete material including cement.

17. A method as defined in claim 1, wherein the concrete structure under test is a bridge.

18. A method as defined in claim 1, wherein the concrete structure under test includes a roadway.

19. A system for estimating degradation and durability characteristics of a concrete structure under test, the concrete structure under test being a reinforced concrete structure, said system comprising:
   a) a set of inputs for receiving information associated with the concrete structure under test;
   b) a concrete degradation simulation unit for processing the information received at the set of inputs for estimating degradation and durability characteristics of the concrete structure under test, said concrete degradation simulation unit being programmed for:
      i) receiving through the set of inputs location-dependent information associated with the concrete structure under test and conveying structural information associated with different locations along the concrete structure under test, the location-dependent information having been obtained by applying a non-destructive testing (NDT) process to the concrete structure under test;
      ii) processing the location-dependent information associated with the concrete structure under test in combination with:
         (1) information conveying material properties associated with the concrete structure under test; and
         (2) information conveying estimated environmental conditions to which the concrete structure under test is subjected;
      the processing being for deriving concrete degradation simulation data, the derived concrete degradation simulation data information conveying estimated degradation and durability characteristics associated with at least some of the different locations along the concrete structure under test;
      iii) releasing a result signal conveying the estimated degradation and durability characteristics of the concrete structure under test;
   c) a display device for displaying information conveying degradation and durability characteristics of the concrete structure under test based on the result signal released by the concrete degradation simulation unit.

20. A system as defined in claim 19, wherein the concrete degradation simulation data conveys current estimated degradation and durability characteristics associated with the different locations along the concrete structure under test.

21. A system as defined in claim 19, wherein the concrete degradation simulation data conveys an evolution over a time period of the estimated degradation and durability characteristics associated with the different locations along the concrete structure under test.

22. A system as defined in claim 21, wherein the time period is specified by a user of the system.

23. A system as defined in claim 19, wherein at least a portion of the information conveying material properties associated with the concrete structure is derived based on analysis applied to a set of cores extracted from the concrete structure under test.

24. A system as defined in claim 19, wherein the information conveying estimated environmental conditions to which the concrete structure under test is subjected conveys temperature information.

25. A system as defined in claim 19, wherein the information conveying estimated environmental conditions to which the concrete structure under test is subjected conveys information related to humidity levels.

26. A system as defined in claim 19, wherein the structural information associated with different locations along the concrete structure under test and conveyed by the location-dependent information includes at least one of:
- location and surface area of delaminated material;
- location and quantity of reinforcing steel;
- location of current corrosion activity;
- location of voids; and
- location and depth of existing repaired portions of the concrete structure under test.

27. A system as defined in claim 19, wherein the NDT process applied to derive the location-dependent information associated with the concrete structure under test includes using ground penetrating radar on the different locations along the concrete structure under test to derive the location-dependent information.

28. A system as defined in claim 19, wherein the concrete structure under test is comprised in part of concrete material including cement.

29. A system as defined in claim 19, wherein the concrete structure under test is a bridge.

30. A system as defined in claim 19, wherein the concrete structure under test includes a roadway.

31. A computer program product, tangibly stored on one or more tangible computer readable storage media, for estimating degradation and durability characteristics of reinforced concrete structures, the computer program product comprising instructions that, when executed, cause a programmable system including at least one programmable processor to perform operations, said operations comprising:
   a) receiving location-dependent information associated with the concrete structure under test and conveying structural information associated with different locations along the concrete structure under test, the location-dependent information having been obtained by applying a non-destructive testing (NDT) process to the concrete structure under test;
   b) processing the location-dependent information associated with the concrete structure under test in combination with:
      i) information conveying material properties associated with the concrete structure under test; and
      ii) information conveying estimated environmental conditions to which the concrete structure under test is subjected;
   the processing being for deriving concrete degradation simulation data, the derived concrete degradation simulation data information conveying estimated degradation and durability characteristics associated with at least some of the different locations along the concrete structure under test;

c) releasing a signal for causing the estimated degradation and durability characteristics of the concrete structure under test to be displayed on a display device in communication with the system.

32. A computer program product as defined in claim 31, wherein the concrete degradation simulation data conveys current estimated degradation and durability characteristics associated with the different locations along the concrete structure under test.

33. A computer program product as defined in claim 31, wherein the concrete degradation simulation data conveys an evolution over a time period of the estimated degradation and durability characteristics associated with the different locations along the concrete structure under test.

34. A computer program product as defined in claim 33, wherein the time period is specified by a user of the system.

35. A computer program product as defined in claim 24, said operations further comprise receiving from a user interface device information conveying the time period.

36. A computer program product as defined in claim 31, wherein at least a portion of the information conveying material properties associated with the concrete structure is derived based on analysis applied to a set of cores extracted from the concrete structure under test.

37. A computer program product as defined in claim 31, wherein the information conveying estimated environmental conditions to which the concrete structure under test is subjected conveys temperature information.

38. A computer program product as defined in claim 31, wherein the information conveying estimated environmental conditions to which the concrete structure under test is subjected conveys information related to humidity levels.

39. A computer program product as defined in claim 31, wherein the information conveying estimated environmental conditions to which the concrete structure under test is subjected conveys information related to exposure to aggressive agents.

40. A computer program product as defined in claim 31, wherein the structural information conveyed by the location-dependent information conveys a state of the materials out of which the concrete structure under test is built.

41. A computer program product as defined in claim 31, wherein the structural information associated with different locations along the concrete structure under test and conveyed by the location-dependent information includes at least one of:
    location and surface area of delaminated material;
    location and quantity of reinforcing steel;
    location of current corrosion activity;
    location of voids; and
    location and depth of existing repaired portions of the concrete structure under test.

42. A computer program product as defined in claim 31, wherein the NDT process applied to derive the location-dependent information associated with the concrete structure under test includes using ground penetrating radar on the different locations along the concrete structure under test to derive the location-dependent information.

43. A computer program product as defined in claim 31, wherein the concrete structure under test is comprised in part of concrete material including cement.

44. A computer program product as defined in claim 31, wherein the concrete structure under test is a bridge.

45. A computer program product as defined in claim 31, wherein the concrete structure under test includes a roadway.

46. Use of a method as defined in claim 1 in an asset managing system for estimating degradation and durability characteristics of a reinforced concrete structure, wherein the reinforced concrete structure is one of a bridge, a port and a roadway.

* * * * *